United States Patent
Alderson

(10) Patent No.: US 12,053,540 B2
(45) Date of Patent: *Aug. 6, 2024

(54) ANTIMICROBIAL COMPOSITIONS CONTAINING SOLVENTS INCLUDING A C3-C5 N-ALKYL-GAMMA-BUTYROLACTAM

(71) Applicant: Virox Technologies Inc., Oakville (CA)

(72) Inventor: Faraz A. Alderson, Oakville (CA)

(73) Assignee: VIROX TECHNOLOGIES INC., Oakville (CA)

(*) Notice: Subject to any disclaimer, the term of this patent is extended or adjusted under 35 U.S.C. 154(b) by 75 days.

This patent is subject to a terminal disclaimer.

(21) Appl. No.: 17/408,598

(22) Filed: Aug. 23, 2021

(65) Prior Publication Data

US 2021/0393497 A1    Dec. 23, 2021

Related U.S. Application Data

(63) Continuation-in-part of application No. 16/830,539, filed on Mar. 26, 2020, now Pat. No. 11,129,385, which is a continuation of application No. PCT/CA2019/051740, filed on Dec. 4, 2019.

(60) Provisional application No. 62/774,964, filed on Dec. 4, 2018.

(51) Int. Cl.

| | |
|---|---|
| A61K 8/49 | (2006.01) |
| A01N 25/02 | (2006.01) |
| A01N 25/22 | (2006.01) |
| A01N 25/30 | (2006.01) |
| A01N 43/36 | (2006.01) |
| A01P 1/00 | (2006.01) |
| A61K 8/365 | (2006.01) |
| A61K 8/368 | (2006.01) |
| A61Q 17/00 | (2006.01) |
| A61Q 19/10 | (2006.01) |

(52) U.S. Cl.
CPC ............ *A61K 8/4913* (2013.01); *A01N 25/02* (2013.01); *A01N 25/22* (2013.01); *A01N 25/30* (2013.01); *A01N 43/36* (2013.01); *A01P 1/00* (2021.08); *A61K 8/365* (2013.01); *A61K 8/368* (2013.01); *A61Q 17/005* (2013.01); *A61Q 19/10* (2013.01); *A61K 2800/52* (2013.01)

(58) Field of Classification Search
CPC ...... A61K 8/4913; A61K 8/365; A61K 8/368; A61K 2800/52; A01N 25/02; A01N 25/22; A01N 25/30; A01N 43/36; A01P 1/00; A61Q 17/005; A61Q 19/10

See application file for complete search history.

(56) References Cited

U.S. PATENT DOCUMENTS

| | | |
|---|---|---|
| 4,132,781 A | 1/1979 | Stoughton |
| 4,305,749 A | 12/1981 | Mildenberger et al. |
| 4,782,078 A | 11/1988 | Crawford et al. |
| 4,885,371 A | 12/1989 | Tracy et al. |
| 5,035,859 A | 7/1991 | Gu et al. |
| 5,130,124 A | 7/1992 | Merianos et al. |
| 5,422,073 A | 6/1995 | Mowrey-McKee et al. |
| 5,762,719 A | 6/1998 | D'Muhala et al. |
| 5,972,237 A | 10/1999 | Muller et al. |

(Continued)

FOREIGN PATENT DOCUMENTS

| | | |
|---|---|---|
| CA | 2 007 239 | 7/1990 |
| CN | 103191050 | 7/2013 |

(Continued)

OTHER PUBLICATIONS

De Schouwer et al., "Bio-based N-alkyl-2-pyrrolidones . . . decarboxylation of glutamic acid", Green Chem., 2017, 19, 4919-4929.

(Continued)

*Primary Examiner* — Sarah Alawadi
*Assistant Examiner* — Thurman Wheeler
(74) *Attorney, Agent, or Firm* — Clark & Brody LP

(57) ABSTRACT

An antimicrobial composition comprising (i) an effective amount of a first antimicrobial agent consisting of at least one solvent which is a compound according to Formula 1:

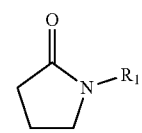

[Formula 1]

wherein $R_1$ is a branched or unbranched, saturated or unsaturated, unsubstituted C3 to C5 alkyl chain or a C3 alkyl chain substituted with a methoxy group; (ii) at least one additional solvent (e.g. selected from the group consisting of ethanol, propanol, butanol, phenethyl alcohol, isopropyl alcohol, benzyl alcohol, phenoxyethanol, cyclopentylmethanol, dimethyl adipate, dimethyl succinate, ethylhexylglycerin, 2-butoxyethanol, diethylene glycol monobutyl ether, ethylene carbonate, propylene carbonate, butylene carbonate, glycerin carbonate, and butyl 3-hydroxybutyrate); and (iii) a diluent, q.s. to 100; wherein the antimicrobial composition is substantially free of peroxygen compounds, antibiotics, and chloroacetamide. Also described are methods of using the compound of Formula 1 and compositions containing same in the field of infection control and prevention.

19 Claims, No Drawings

(56) References Cited

U.S. PATENT DOCUMENTS

| | | | |
|---|---|---|---|
| 6,017,863 A | 1/2000 | Cala et al. | |
| 6,100,227 A | 8/2000 | Burlew | |
| 6,828,277 B2 | 12/2004 | Manzer | |
| 7,419,944 B2 | 9/2008 | Mowrey-McKee et al. | |
| 7,485,619 B2 | 2/2009 | Kim et al. | |
| 7,666,823 B2 | 2/2010 | Minick | |
| 8,268,763 B2 | 9/2012 | Lane et al. | |
| 8,865,196 B2 * | 10/2014 | Omidbakhsh | A01N 37/36 424/405 |
| 9,167,812 B2 | 10/2015 | Bigorra Llosas | |
| 2004/0192933 A1 | 9/2004 | Manzer et al. | |
| 2007/0270612 A1 | 11/2007 | Pompeo et al. | |
| 2008/0095863 A1 | 4/2008 | Kabra | |
| 2018/0002645 A1 | 1/2018 | Bartley et al. | |
| 2018/0055048 A1 | 3/2018 | Premachandran | |
| 2019/0330489 A1 | 10/2019 | Dukhopelnikov | |

FOREIGN PATENT DOCUMENTS

| | | | |
|---|---|---|---|
| GB | 1 169 113 | | 10/1969 |
| GB | 1525120 | | 9/1978 |
| JP | 73003394 | | 1/1973 |
| JP | H10-330792 | * | 12/1998 |
| JP | 2007-031299 | | 2/2007 |
| WO | 95/21238 | | 8/1995 |
| WO | 1996/02624 | | 2/1996 |
| WO | 2002/50225 | | 6/2002 |
| WO | 2002/50241 | | 6/2002 |
| WO | WO2002/050225 | * | 6/2002 |
| WO | 2003/006046 | | 1/2003 |
| WO | 2003/094920 | | 11/2003 |
| WO | 2004/074417 | | 9/2004 |
| WO | 2006/005551 | | 1/2006 |
| WO | 2008/031104 | | 3/2008 |
| WO | 2008/052031 | | 5/2008 |
| WO | 2011/146182 | | 11/2011 |
| WO | 2013/107822 | | 1/2013 |
| WO | WO2015/017175 | * | 2/2015 |

OTHER PUBLICATIONS

Ansell et al., "The Acute Oral . . . of Selected N-Alkyl-2-Pyrrolidones", Food and Chemical Toxicology, vol. 26, No. 5, pp. 475-479, 1988.

Phaechamud et al., "Characterization and Antimicrobial . . . Copolymer Thermosensitive Gel", Indian Journal of Pharmaceutical Sciences, vol. 74, No. 6, Jan. 1, 2012.

Gaonkar et al., (In Vivo Efficacy of an Alcohol-based Surgical Hand Disinfectant Containing a Synergistic Combination of Ethylhexylglycerin and Preservatives). (Year 2006).

Search Report and International Application in International Application No. PCT/IB2019/059671 dated Jan. 14, 2020, 8 pages.

Dhavan et al., "Antibacterial and Antifungal Activities of 2,3,-pyrrolidinedione Derivatives Against Oral Pathogens", Bioorganic and Medicinal Chemistry letters, vol. 26(5), Feb. 4, 2016, 11 pages.

Zeng et al., "Antifungal Activities of €-4-benzylidene-5 oxopyrrolidine-2carboxamides and 6-oxo-1,2,3,6-tetrahydropyridin-2-carboxamides Synthezed via Ugi Reaction From Baylis-hillman Bromides", 2nd International Conference on Agricultural and Biological Sciences (ABS 2016): IOP Conference Series: Earth and Environmental Science, vol. 41, 2016, pp. 1-5.

Hosseinzadeh et al., "An Overview on Chemistry and Biological Importance of Pyrrolidinone", Current Organic Synthesis, vol. 14, 2017, 14 pages.

Cardinal Intellectual Property, Patent Search Report, Patentability Search, "Antimicrobial Compositions for Use in Sanitization, Disinfection and Sterilization of Various Surf", Oct. 24, 2018, 13 pages.

Search Report in International Application No. PCT/CA2019/051740 dates Jan. 31, 2020.

\* cited by examiner

ANTIMICROBIAL COMPOSITIONS CONTAINING SOLVENTS INCLUDING A C3-C5 N-ALKYL-GAMMA-BUTYROLACTAM

This application is a continuation-in-part of U.S. application Ser. No. 16/830,539 filed Mar. 26, 2020, which is a continuation of international application no. PCT/CA2019/051740 filed Dec. 4, 2019, which in turn claims the benefit of and priority from U.S. provisional application 62/774,964 filed on Dec. 4, 2018 under 35 U.S.C. 119(d), the entire respective contents of which applications are incorporated herein by reference.

FIELD OF THE DISCLOSURE

The present specification relates to antimicrobial compositions and methods of using same in the field of infection control and prevention, e.g. for sanitization, disinfection and/or sterilization.

BACKGROUND OF THE DISCLOSURE

There is an ongoing effort to develop antimicrobial compositions that are effective against microorganisms, low in toxicity to humans and other animals, and not harmful to the environment.

Known antimicrobial agents include linear and cyclic carboxylic acids, certain types of organic solvents, anionic surfactants, amphoteric surfactants, quaternary ammonium compounds, phenols, aldehydes, biguanides, terpenes, essential oils, mineral acids, halogen compounds, and antimicrobial metals such as copper, and mixtures thereof. The benefits of using antimicrobial organic solvents are that they can enhance soil removal and evaporate to leave no antimicrobial active residues on the surface.

While antimicrobial compositions employing a variety of antimicrobial agents are known, there is an ongoing need to provide new and improved antimicrobial compositions that are environmentally friendly, non-toxic, and efficacious.

SUMMARY OF THE DISCLOSURE

Surprisingly, the inventor has found that a class of solvents, namely C3-C5 N-alkyl-gamma-butyrolactams, possess antimicrobial properties and can be used alone as the sole antimicrobial agent in an antimicrobial composition, or to synergistically enhance the antimicrobial activity of solutions containing other antimicrobial agents. An example solvent is N-butyl-gamma-butyrolactam where the alkyl group has four carbon atoms. Surprisingly, these compounds are also effective against hard-to-kill microbes such as mycobacteria. Also surprisingly, the inventor has found additional synergies between and amongst other antimicrobial agents disclosed herein in solutions containing a C3-C5 N-alkyl gamma-butyrolactam.

Thus, according to a first aspect, the invention provides an antimicrobial composition comprising, consisting essentially of, or consisting of (i) an effective amount of a first antimicrobial agent consisting of at least one solvent which is a compound according to Formula 1.

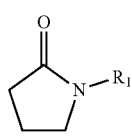

[Formula 1]

wherein $R_1$ is a branched or unbranched, saturated or unsaturated, unsubstituted C3 to C5 alkyl chain or a C3 alkyl chain substituted with a methoxy group; and (ii) a diluent, q.s. to 100; wherein the first antimicrobial agent is effective to reduce the number of microbes on a surface by at least 50% when an effective amount of the antimicrobial composition is applied to the surface for a contact time of 10 minutes, and wherein the composition is substantially free of peroxygen compounds, antibiotics, and chloroacetamide.

The compound according to Formula 1 can be a C4 N-alkyl-gamma-butyrolactam such as N-butyl-gamma-butyrolactam, N-isobutyl-gamma-butyrolactam, and N-methoxypropyl-gamma-butyrolactam.

The antimicrobial composition can further comprise, consist essentially of, or consist of an effective amount of at least one solvent other than the compound of Formula 1, which can be selected from the group consisting of alcohols, dibasic esters, branched and unbranched diol solvents, glycol ethers, carbonates, and butyl 3-hydroxybutyrate.

In some embodiments, the at least one solvent is selected from the group consisting of C1-C8 alcohols, cyclic alcohols, dialkyl adipates, dialkyl glutarates, dialkyl succinates, phenols, and glyceryl ethers. In the same or other embodiments, the at least one solvent can be selected from the group consisting of ethanol, propanol, butanol, phenethyl alcohol, isopropyl alcohol, benzyl alcohol, phenoxyethanol, cyclopentylmethanol, dimethyl adipate, dimethyl succinate, ethylhexylglycerin, 2-butoxyethanol, diethylene glycol monobutyl ether, ethylene carbonate, propylene carbonate, butylene carbonate, glycerin carbonate, and butyl 3-hydroxybutyrate. Surprisingly, some of these solvents have also been found to be synergistic with the compound of Formula 1. In certain embodiments, at least one, two three, four or five of the aforementioned solvents are present.

The antimicrobial composition can further comprise, consist essentially of, or consist of at least one additional antimicrobial agent selected from the group consisting of carboxylic acids and salts thereof, anionic surfactants, amphoteric surfactants, quaternary ammonium compounds, aldehydes, biguanides, mineral acids, and antimicrobial metals. Some of these additional antimicrobial agents have also been found to (surprisingly) synergistically enhance the antimicrobial activity of the present compositions.

Examples of carboxylic acids and salts thereof useful in the present compositions include formic acid, benzoic acid, salicylic acid, 2-furoic acid, mandelic acid, acetic acid, dimethylol propionic acid, gallic acid, malic acid, lactic acid, citric acid, sulfosalicylic acid, sulfosuccinic acid, glycolic acid, oxalic acid, propionic acid, maleic acid, ascorbic acid, neopentanoic acid, malonic acid, succinic acid, glutaric acid, and salts thereof. Formic acid, benzoic acid, salicylic acid, 2-furoic acid, mandelic acid, acetic acid, dimethylol propionic acid, gallic acid, malic acid, lactic acid, and salts thereof have been found to act synergistically with N-butyl-gamma-butyrolactam. Furthermore, citric acid has been found to synergistically enhance the antimicrobial activity of compositions containing a cyclic carboxylic acid (e.g. 2-furoic acid) and N-butyl-gamma-butyrolactam. Thus, certain embodiments will have one or more of these acids and/or salts thereof. In the same or other embodiments, at least one of citric acid and/or salts thereof will be present on their own or alongside at least one cyclic carboxylic acid and/or salt thereof, such as benzoic acid, salicylic acid, 2-furoic acid, and mandelic acid, and salts thereof.

In certain embodiments, at least one, two, three, four or five of the aforementioned carboxylic acids and/or salts thereof are present.

The anionic surfactants can be selected from the group consisting of alkyl sulfuric acids, alkyl ether sulfuric acids, alkyl sulfonic acids, alkyl aryl sulfonic acids, alkyl phosphoric acid esters, alkyl carboxylic acids, alkyl ether carboxylic acids, acylamino acids, and salts thereof. These surfactants are expected to enhance at least one of the antimicrobial and detersive properties of the composition, which may be beneficial when disinfecting soiled surfaces.

The antimicrobial composition can further comprise, consist essentially of, or consist of at least one ingredient selected from the group consisting of chelating agents, stabilizing agents, pH adjusting agents, buffering agents, preservatives, nonionic surfactants, cationic surfactants, amphoteric surfactants, hydrotropes, skin conditioning agents, anti-foaming agents, builders, soil suspenders, anti-redeposition agents, brightening agents, radical scavengers, dyes, fragrances, rheology modifiers, emulsifiers, corrosion inhibitors, softening agents, anti-static agents, anti-wrinkling agents, dye transfer inhibition agents, color protection agents, odor removal agents, odor capturing agents, soil shielding agents, soil releasing agents, ultraviolet light protection agents, water repellency agents, insect repellency agents, anti-pilling agents, souring agents, mildew removing agents, film-forming agents, plasticizers, and allergicides. The at least one ingredient can also be selected from the group consisting of chelating agents, pH adjusting agents, buffering agents, nonionic surfactants, amphoteric surfactants, skin conditioning agents, hydrotropes, corrosion inhibitors, and fragrances.

The present invention contemplates both ready-to-use (RTU) antimicrobial compositions as well as concentrated versions thereof. The amount of diluent present will determine the concentration of the compounds or ingredients in solution. Reducing the amount of diluent in the composition will provide a more concentrated solution which can be diluted by the end user at the time of use to form a ready-to-use (RTU) solution. The diluent can be an aqueous or a non-aqueous diluent. An example of an aqueous diluent is water. An example of non-aqueous diluent is a non-aqueous solvent, such as propylene glycol. When water is present, the compositions can further comprise, consist essentially of, or consist of a pH adjusting agent (e.g. NaOH, KOH, phosphoric acid, hydrochloric acid, etc.).

The present antimicrobial compositions are to be distinguished from preservatives which may be included therein. Preservatives are microbistatic compounds that prevent microbial growth of microbes in a medium or end-use product, such as cosmetic lotions, cleaning formulations, paints, etc. On the other hand, the present compositions are microbicidal and designed to kill microbes rather than prevent their growth.

According to a second aspect, the invention provides a method of synergistically enhancing the antimicrobial activity of an antimicrobial composition, wherein the antimicrobial composition comprises (i) an effective amount of at least one solvent selected from the group consisting of ethanol, propanol, butanol, phenethyl alcohol, isopropyl alcohol, benzyl alcohol, phenoxyethanol, cyclopentylmethanol, dimethyl adipate, dimethyl succinate, ethylhexylglycerin, 2-butoxyethanol, diethylene glycol monobutyl ether, ethylene carbonate, propylene carbonate, butylene carbonate, glycerin carbonate, and butyl 3-hydroxybutyrate; and wherein the method comprises adding to the antimicrobial composition an effective amount of at least one compound according to Formula 1.

The method can further comprise adding additional compounds to further boost or synergistically boost the antimicrobial activity of the antimicrobial composition. These additional compounds can be selected from the group consisting of the aforementioned carboxylic acids and salts thereof, anionic surfactants, amphoteric surfactants, quaternary ammonium compounds, aldehydes, biguanides, mineral acids, certain glycerol ethers, antimicrobial metals, and certain nonionic surfactants.

A third aspect of the invention provides a method of reducing the microbial load on a surface contaminated with microbes, the method comprising (a) identifying a surface in need of microbial reduction, and (b) applying an effective amount of an antimicrobial composition according to the first aspect to the surface for a time (the "contact time") and at a temperature sufficient to reduce the microbial load by at least 50%.

In some embodiments, the contact time can range from about 10 seconds to about 10 minutes, e.g. from about 10, 30, 45, or 60 seconds and up to about 10, 9, 8, 7, 6, 5, 4, 3, 2 or 1 minute(s).

The microbes can be selected from the group consisting of bacteria, viruses, viroids, fungi, yeasts, mycobacteria, fungal spores, bacterial spores, phages, prions, protozoa, parasites, and combinations thereof. In some embodiments, the microbes include mycobacteria and/or bacteria.

In certain embodiments, the method is performed at a temperature ranging from about −20° C., −15° C., −10° C., −5° C., 0° C. or 5° C. and up to about 80° C., 75° C., 70° C., 65° C., 60° C., 55° C., 50° C., 45° C., 40° C., 35° C. or 30° C. Furthermore, the method can be employed at an atmospheric pressure of from about 0, 5, 10, or 15 PSI units and up to about 50, 45, 40, or 35 PSI units.

For the purpose of this disclosure, successful microbial reduction is achieved when the microbial populations are reduced by at least about 50% in 10 minutes. A 50% reduction in microbial load is equivalent to about 0.3 log base ten reduction. Larger reductions in microbial population will provide greater levels of protection. Depending on the identity of ingredients or compounds in the composition, their concentrations, contact time employed, temperature, and identity of the microbes, the microbial load can be reduced by at least 1 $\log_{10}$, 2 $\log_{10}$, 3 $\log_{10}$, 4 $\log_{10}$, or 5 $\log_{10}$. The person skilled in the art will be able to make sanitizers, disinfectants and sterilants according to the first aspect of the present invention based on the teachings herein.

Antimicrobial compositions comprising, consisting essentially of, or consisting of the at least one C3-C5 N-alkyl-gamma-butyrolactam can be applied to both hard and soft surfaces present a wide range of settings including agricultural, commercial, industrial, institutional (e.g. human and animal health care institutions such as hospitals, medical clinics, dental offices, veterinary hospitals and clinics, etc.), and residential settings. These surfaces include, without limitation, surfaces of tools, instruments, eating and cooking utensils, dishes, machinery, devices, articles, equipment, apparatus, vehicles, countertops, sinks, showers, bathtubs, toilets, windows, mirrors, appliances, furniture, cabinetry, floors, walls, fixtures, buildings, other structures, fabric surfaces, e.g., knit, woven, and non-woven surfaces (such as surgical garments, draperies, bed linens, bandages, etc.), skin, fur, plants, plant products, food products, meat products, poultry, poultry debris, and soil. The treated surfaces can be left to dry naturally, dried actively using a medium, or rinsed off using water or other agents. When applied to food products, they must be rinsed before consumption.

The surfaces can be made of plastic including, without limitation, polycarbonate polymers (PC), acrilonitrile-butadiene-styrene polymers (ABS), polysulfone polymers (PS), and polyethylene terephthalate (PET).

The present compositions can be formulated into different formats, such as in the form of a clear solution, emulsion, gel, foam, cream, or slurry, and can be applied using various machines, devices or articles such as, without limitation, a manually actuated trigger spray, aerosol canister, bag-on-valve canister, fogging device, misting device, foaming device, pre-moistened wipe substrate, mopping device, soaking container, ultrasonic bath, automated washing apparatus, ionizing spray, electrostatic spray, electrolyzing spray, steamer, cold plasma generating device, automated dilution device, and laundering machine. Furthermore, various critical and non-critical medical devices and articles can be submerged in the compositions of this invention while at atmospheric pressures, higher than atmospheric pressures, lower than atmospheric pressures, or under vacuum. A critical medical device is a device that penetrates the skin or mucous membranes, has contact with blood and or body fluids, or enters normally sterile cavities and therefore presents a high risk of infection if the medical device is contaminated with any organisms, including bacterial spores. A non-critical medical device is a medical device, other than a critical medical device.

The invention will now be described in further detail including with reference to examples.

DETAILED DESCRIPTION OF THE DISCLOSURE

For the sake of clarity and to avoid ambiguity, certain terms are defined herein as follows.

The term "comprising" means "including without limitation." Thus, a composition comprising a list of ingredients may include additional ingredients not expressly recited. The term "consisting of" means "including the listed ingredients and such additional ingredients as can be present in the listed ingredients as natural or commercial impurities or additives." Natural and commercial impurities and additives will be apparent to the person of ordinary skill in the art. The term "consisting essentially of" means "consisting of" the listed ingredients (as defined herein) and additional ingredients that would not "materially affect" the basic and novel properties of the composition." By "basic and novel properties" is meant the ability of the antimicrobial composition to reduce the microbial load on a surface contaminated with microbes. For the sake of clarity, a change in efficacy (positively or negatively) of greater than 0.3 log using ASTM E2197-02 test method against $S.\ aureus$, at a contact time of up to about 10 minutes, at 20-25° C., is deemed herein to constitute a "material effect."

The term "weight percent," "wt. %," "percent by weight," "% by weight," "% wt.," and variations thereof, refer to the concentration of a substance as the weight of that substance divided by the total weight of the composition containing that substance, and multiplied by 100.

The term "about" refers to variations in an expressed numerical quantity that can occur, for example, through measuring and liquid handling procedures used for making concentrates or ready-to-use (RTU) solutions in the real world, differences in the manufacture, source, or purity of the ingredients used to make the compositions or carry out procedures, and differences due to different equilibrium conditions or different reaction levels for a composition resulting from an initial mixture. For the sake of clarity, the term "about" includes variations in the expressed value of ±5%. Whether a value is modified by the term "about," the specification includes equivalents to the values. Notwithstanding the foregoing, the term "about" includes variations to the expressed value of ±0.5% for any value expressed on a logarithmic scale such as pH.

When used herein, the term "effective amount" means an amount that would bring about a desired effect, based on the purpose and function of the compound or ingredient and composition in which the compound or ingredient is used. What constitutes an effective amount will be determinable by the person of ordinary skill in the art without having to engage in inventive experimentation. For example, an effective amount of a pH adjusting agent is that amount which would cause the pH of the solution to reach a desired value. An "effective amount" of an antimicrobial agent means an amount that, together with other ingredients in a composition, will cause the composition to achieve the desired level of antimicrobial efficacy based on the intended application.

In the description and claims, the singular forms "a," "an," and "the" include plural referents unless the context clearly dictates otherwise. Thus, for example, reference to a composition containing "a compound" includes a composition having two or more compounds. It should also be noted that the term "or" is generally employed in the sense of "and/or" unless the context clearly dictates otherwise.

The ranges of values recited herein are intended to include all values within the ranges. Thus, for example, a range of 0.01 to 4.5 wt. % is intended to include values such as from 0.02, 0.03, or 0.04, etc. wt. % and up to 4.4, 4.3, or 4.2, etc. wt. %.

The term "microbial load" means the amount of microorganisms present on a surface to be disinfected. As used herein, the term "microorganism" refers to any non-cellular or unicellular (including colonial) organism. Microorganisms include bacteria (including cyanobacteria and mycobacteria), spores, lichens, fungi, protozoa, viruses, viroids, phages, prions, and some algae. As used herein, the term "microbe" is synonymous with microorganism.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leaves, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the phrase "plant" or "plant product" includes any plant substance or plant-derived substance. Plant products include, but are not limited to, seeds, nuts, nut meats, cut flowers, plants or crops grown or stored in a greenhouse, house plants, and the like. Plant products include many animal feeds.

As used herein, the phrase "meat product" refers to all forms of animal flesh, including the carcass, muscle, fat, organs, skin, bones and body fluids and like components that form the animal. Animal flesh includes, but is not limited to, the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "poultry debris" refers to any debris, residue, material, dirt, offal, poultry part, poultry waste, poultry viscera, poultry organ, fragments or combinations of such materials, and the like removed from a poultry carcass or portion during processing and that enters a waste stream.

As used herein, the term "instrument" refers to the medical and dental instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present specification. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressers, trocars, dilators, cages, glassware, tubing, catheters, cannulas, plugs, stents, scopes (e.g., endoscopes, stethoscopes, and arthroscopes) and related equipment, or any other devices that can benefit from treatment with an antimicrobial composition according to the present specification.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, the term "sanitizer" refers to an agent that reduces the number of bacterial contaminants to safe levels as judged by public health requirements. Sanitizers are defined herein as compositions that can provide at least a 99.9% reduction of live microbial cells (3-log order reduction). As used herein, the term "disinfectant" refers to an agent that reduces the number of bacterial contaminants to safer levels as judged by public health requirements. Disinfectants are defined herein to mean a composition that can provide at least a 99.999% reduction of live microbial cells (5-log order reduction). As used herein, the term "sterilant" refers to an agent that inactivates the entire microbial load on a given surface. These reductions can be evaluated using a variety of different antimicrobial efficacy testing methods, as required by specific regulatory agencies such as Unites States Environmental Protection Agency, Health Canada, and Biocidal Products Regulation of the European Union.

As used herein, the term "q.s." means "quantum sufficit" or "quantum satis" a Latin term meaning the amount which is enough, or standard pharmaceutical meaning of "as much as is sufficient".

When used herein, the term "substantially free" in relation to a compound means that the compound is either not present or is present in a concentration of less than about 0.1% wt. The skilled person will appreciate that a compound may be present as impurities resulting from impurities in raw materials used to make the compositions or from reactions between and amongst ingredients in raw materials used to make the compositions.

As used herein, the term "synergistic" or "synergy" refers to a result that is more than merely additive. For example, if 'Solution 1' containing 1% of antimicrobial Agent-A demonstrates a bacterial $\log_{10}$ reduction of 0.5, and 'Solution 2' containing 1% of antimicrobial Agent-B demonstrates a bacterial $\log_{10}$ reduction of 0.5, then 'Solution 3' containing 1% of each of Agent-A and Agent-B would only be synergistic if it demonstrates a bacterial $\log_{10}$ reduction of greater than 1.

As used herein, the term "alkyl" or "alkyl groups" refers to saturated or unsaturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonate, phosphine, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sultanates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups can be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The chemical structures herein are drawn according to the conventional standards known in the art. Thus, where an atom, such as a carbon atom, as drawn appears to have an unsatisfied valency, then that valency is assumed to be satisfied by a hydrogen atom, even though that hydrogen atom is not necessarily explicitly drawn. The structures of some of the compounds of this invention include stereogenic carbon atoms. It is to be understood that isomers arising from such asymmetry (e.g., all enantiomers and diastereomers) are included within the scope of this invention unless indicated otherwise. That is, unless otherwise stipulated, any chiral carbon center can be of either (R) or (S) stereochemistry. Such isomers can be obtained in substantially pure form by classical separation techniques and by stereochemically-controlled synthesis. Furthermore, alkenes can include either the E- or Z-geometry, where appropriate. In addition, the compounds of the present specification may exist in unsolvated as well as solvated forms with acceptable solvents such as water, propylene glycol, ethanol, and the like. In general, the solvated forms are considered equivalent to the unsolvated forms for the purposes of the present specification.

The present specification contemplates the possibility of omitting any components listed herein even though they are not expressly named as included or excluded from the invention.

C3-C5 N-Alkyl-Gamma-Butyrolactams

The C3-C5 N-alkyl-gamma-butyrolactam family of compounds are represented by the following formula:

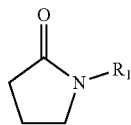

[Formula 1]

wherein R1 is a branched or unbranched, saturated or unsaturated, unsubstituted C3-C5 alkyl chain or a C3 alkyl chain substituted with a methoxy group. These compounds include N-propyl-gamma-butyrolactam, N-isopropyl-gamma-butyrolactam, N-butyl-gamma-butyrolactam, N-pentyl-gamma-butyrolactam, and N-isopentyl-gamma-butyrolactam. Other variants of N-alkyl-gamma-butyrolactam can include, without limitation, N-isobutyl-gamma-butyrolactam, and N-methoxypropyl-gamma-butyrolactam.

C3-C5 N-alkyl-gamma-butyrolactam compounds are known to be polar aprotic solvents possessing high chemical and thermal stability. They are normally used to provide solvency for a wide range of compounds. Other known uses include applications in specialty polymer coatings (wire enamels & coated cooking gear), micro-electronics manufacturing (photoresist stripper), other coatings (waterborne polyurethane dispersions), paint strippers and inks, chemical synthesis and agrochemical formulations. See, for example, US 2015/0057375 A1 to Vandeputte et al. which is incorporated herein by reference.

There is literature teaching the use of N-alkyl pyrrolidones in compositions for treating medical conditions or diseases. For example, U.S. Pat. No. 4,132,781, which is incorporated herein by reference, teaches a topical antibacterial composition and method for treatment of acne. The composition taught therein contains an antibiotic of the erythromycin family and 2-pyrrolidone or an N-lower alkyl-2-pyrrolidone. GB1525120, which is incorporated herein by reference, teaches topical antimicrobial compositions for the treatment of acne comprising 0.1 to 10% by weight of an antibiotic selected from griseofulvin and erythromycin or lincomycin together with 5 to 99.9% by weight of 2-pyrrolidone or an N-alkyl-2-pyrrolidone. As will be appreciated by a person of skill in the art, these references are directed to treatment of a medical condition and require the use of the antibiotics cited therein. The antibiotics disclosed the aforementioned prior art references are excluded from compositions according to the first aspect of the invention.

Surprisingly, the inventor has found that C3-C5 N-alkyl-gamma-butyrolactam compounds possess antimicrobial activity making them useful in antimicrobial compositions for reducing the microbial load on a surface contaminated with microbes. These compounds can be used "straight" (100 wt. % concentration) to reduce the microbial load on a surface, or combined with other ingredients, e.g. a diluent and/or additional ingredients to make an antimicrobial composition.

Also surprisingly, the inventor has found that these compounds can synergistically enhance the antimicrobial activity of an antimicrobial composition that contains one or more additional antimicrobial agents.

In such antimicrobial composition, specifically in a solution, the at least one C3-C5 N-alkyl-gamma-butyrolactam can be present in a concentration of from about 0.1, 0.25, 0.5, 1, 2.5, 5, 7, 9 or 10 wt. % and up to about 99.9, 90, 85, 80, 75, 70, 65, 60, 55, 50, 45, 40, 35, 30, 25, 20, 18, 16, 14 or 12 wt. %. This solvent will generally not be more than about 15 wt. % in ready-to-use solutions, or less than about 4 wt. % in concentrated solutions.

Concentrated versions of solutions containing at least one C3-C5 N-alkyl-gamma-butyrolactam can be diluted by the end user with water or another diluent. In certain embodiments, the concentrated version may be diluted, for example, at a ratio of 1:1, 1:2, 1:4, 1:8, 1:16, 1:32, 1:64, 1:128, 1:256, or 1:512 (composition:diluent) or at other ratios in between these values. The amount of diluent required depends on the desired concentration of the C3-C5 N-alkyl-gamma-butyrolactam in the overall antimicrobial composition.

The present invention also contemplates a kit of parts wherein the at least one C3-C5 N-alkyl-gamma-butyrolactam is present as one part of the kit to be combined with other parts to form an antimicrobial composition according to the first aspect of the invention prior to use.

C3-C5 N-alkyl-gamma-butyrolactams, such as N-butyl-gamma-butyrolactam, possess a mild and agreeable odor and are not toxic to mammals, not highly volatile and are less flammable than their shorter-chained C1 and C2 versions. The C1 and C2 versions (N-methyl pyrrolidone (NMP) and N-ethyl pyrrolidone (NEP)) are known to be toxic to mammals. Accordingly, in some embodiments, the present antimicrobial compositions are substantially free of NMP and NEP. However, one or both of these solvents can be present. It is expected that adding these solvents to the present composition will not negatively impact the composition's synergistic antimicrobial efficacy.

The C3-C5 N-alkyl-gamma-butyrolactams, such as N-butyl-gamma-butyrolactam, are fully soluble in water and other aqueous solutions. In contrast, N-alkyl-gamma-butyrolactams with an alkyl chain length greater than C6 can have low to very low solubility in water. The C3-C5 N-alkyl-gamma-butyrolactams are also more compatible with and safer to use on plastics, resins, and painted surfaces. In contrast, other antimicrobial solvents, such as benzyl alcohol and dimethyl adipate, may be less compatible (depending on their use concentration) for use on some plastic and polymeric surfaces such as acrylics, acetals, and polyurethanes, though they may be effective against mycobacteria.

N-alkyl-gamma-butyrolactams with an alkyl chain length of greater than C6, e.g. C7 to C20 N-alkyl-gamma-butyrolactams, such as octyl-gamma-butyrolactam (trade name: Surfadone™ LP-100), fall under the category of nonionic surfactants and are no longer considered to be solvents. C7 to C20 N-alkyl-gamma-butyrolactams have limited solubility in water due to the longer length of their alkyl chains and hence increased lipophilicity.

Solvents

The present compositions comprise at least one solvent (in addition to the compound of Formula 1) for their antimicrobial, cleaning, and dissolution properties. Some of these solvents are known to have antimicrobial properties, while others are not known to be antimicrobial. Surprisingly, the inventor has found that certain solvents, e.g. butyl-3-hydroxybutyrate, while not known to have antimicrobial properties, can boost the antimicrobial efficacy of antimicrobial compositions according to the invention.

The at least one additional solvent that can be used in the present compositions include, without limitation, linear or branched alcohols (e.g. methanol, ethanol, isopropyl alcohol, N-butanol, tert-butanol, and $C_5$-$C_8$ alcohols); cyclic alcohols (e.g. phenethyl alcohol, benzyl alcohol, phenoxyethanol, cyclopentylmethanol); glyceryl ethers (e.g. ethylhexylglycerin); benzyl acetate; benzyl benzoate; essential oils (e.g. benzaldehyde, pinenes, terpineols, terpinenes, carvone, cinnamealdehyde, borneol and its esters, citrals, ionenes, jasmine oil, limonene, dipentene, linalool and its esters); diester dicarboxylates (also called dibasic esters) (e.g. dialkyl adipates, dialkyl succinates, dialkyl glutarates; more particularly, e.g., dimethyl adipate, dimethyl succinate, dimethyl glutarate, dimethyl malonate, diethyl adipate, diethyl succinate, diethyl glutarate, dibutyl succinate, and dibutyl glutarate, dimethyl sebacate, dimethyl pimelate, and dimethyl suberate); phthalate esters (e.g. dibutyl phthalate, diethylhexyl phthalate, and diethyl phthalate); butyl-3-hydroxybutyrate; acetophenone; dialkyl carbonates (e.g. dimethyl carbonate, diethyl carbonate, dipropyl carbonate, diisopropyl carbonate, and dibutyl carbonate); organo-nitriles (e.g. acetonitrile and benzonitrile); monoalkyl carbonates (e.g. ethylene carbonate, propylene carbonate, butylene carbonate, and glycerin carbonate); 2-acetyl-1-methylpyrrole; propylene glycol derivatives with ethoxylation and/or propoxylation; alkoxytriglycols (e.g. methoxytriglycol, ethoxytriglycol, butoxytriglycol, and hexyltriglycol); glycol solvents (e.g. propylene glycol methyl ether acetate, diethylene glycol monoethyl ether, diethylene glycol monobutyl ether, dipropylene glycol methyl ether acetate, dipropylene glycol n-butyl ether, propylene glycol n-butyl ether, dipropylene glycol n-propyl ether, propylene glycol n-propyl ether, dipropylene glycol methyl ether, tripropylene glycol methyl ether); branched or unbranched diols; some ethoxylated or propoxylated nonionic surfactants; charged or uncharged non-surfactant emulsifying agents; polar protic solvents; and polar aprotic solvents.

In some embodiments, the at least one additional solvent is selected from the group consisting of alcohols, dibasic esters, branched and unbranched diol solvents, glycol ethers, carbonates, and butyl 3-hydroxybutyrate.

In the same or other embodiments, the at least one additional solvent is selected from the group consisting of C1-C8 alcohols, cyclic alcohols, dialkyl adipates, dialkyl glutarates, dialkyl succinates, phenols, and glycerol ethers.

The at least one additional solvent can also be selected from the group consisting of ethanol, propanol, butanol, phenethyl alcohol, isopropyl alcohol, benzyl alcohol, phenoxyethanol, cyclopentylmethanol, dimethyl adipate, dimethyl succinate, ethylhexylglycerin, 2-butoxyethanol, diethylene glycol monobutyl ether, ethylene carbonate, propylene carbonate, butylene carbonate, glycerin carbonate, and butyl 3-hydroxybutyrate.

The at least one additional solvent is present in an effective amount. For example, the at least one additional solvent can be present in a concentration from about 0.05, 0.1, 0.5, 1, 1.5, 2, 2.5, 3, 3.5, 4, 4.5, 5, 5.5, 6, 6.5, 7, 7.5, or 8 wt. % and up to about 70, 65, 60, 55, 50, 45, 40, 35, 30, 25, 20, 15, 12, 10, or 9 wt. %.

The at least one additional solvent will generally not be more than about 20 wt. % in ready-to-use solutions, or more than about 50 wt. % in concentrated solutions. Solvents with a higher evaporation rate than water, such as ethanol, may be used in compositions of this invention at concentrations above 50 wt. %.

Exclusions from the Present Compositions

The present compositions are substantially free of peroxygen compounds, antibiotics such as those disclosed in U.S. Pat. No. 7,485,619 and GB 1525120A, and chloroacetamide (an organo-halogen compound).

The present compositions can also be (optionally) substantially free of other organo-halogen compounds, such as other organo-chlorine compounds, as well as organo-bromine compounds. Furthermore, the present compositions can be (optionally) substantially free of N-methyl pyrrolidone (NMP), N-ethyl pyrrolidone (NEP), the glycosylated mucocidin antimicrobial peptides disclosed in U.S. Pat. No. 7,485,619, dehydroacetic acid (DHA), and certain agricultural plant and crop treatment agents such as alachlor, alpha-cypermethrin, difenoconazole, difenoconazole, glyphosate, oxyfluorfen, pendimethalin, phenmedipham, propanil, propoxur, tebuconazole, triadimenol, and trifluralin.

Peroxygen Compounds

The present compositions are substantially free of peroxygen compounds.

When used herein, a "peroxygen compound" is a compound containing an oxygen-oxygen single bond or the peroxide anion. Examples include alkali metal peroxides (e.g. sodium peroxide). Also included are compounds that generate and release hydrogen peroxide when dissolved in aqueous solution (e.g. urea peroxide, perboric acid, sodium/potassium perborate, sodium persulfate, calcium peroxide, lithium peroxide, sodium peroxide, or other peroxides of alkali, alkaline earth, or transition group metals or salts thereof).

Still other examples are organic compounds containing two oxygens that are connected to each other through a single covalent bond, wherein the second chemical bond on each of the two oxygens attaches them, independently, to an organic moiety. The attached organic moieties can be independently a substituted or unsubstituted, branched or unbranched, saturated or unsaturated, cyclic or linear alkyl group. Examples include dialkyl peroxides such as dibenzoyl peroxide, diacetyl peroxide, di(n-propyl) peroxydicarbonate, butyl peroxybenzoate, and many others commercially available, without limitation, under the brand name Luperox™. In certain cases, at least one of the organic moieties can be sulfur or phosphorus atoms (e.g. peroxidisulfuric acid). In certain examples, one of the two attached organic moieties could be hydrogen. Examples of such molecules include, without limitation, hydrogen peroxide, butyl hydroperoxide, ethylidene peroxide, and ethyl hydroperoxide. In certain cases, at least one of the moieties can be sulfur or phosphorus atoms (e.g. peroximonosulfuric acid). Examples of peroxygen compounds expressly excluded from compositions according to the invention are hydrogen peroxide, sodium peroxide, benzoyl peroxide, dibenzyl peroxides, percarbonates (e.g. sodium percarbonates, potassium percarbonates), peroxymonosulfuric acid, and peroxydisulfuric acid.

Optional Additional Ingredients

Depending on the application and properties that are desired for the antimicrobial composition, additional ingredients can be included such as at least one ingredient selected from the group consisting of additional antimicrobial agents, chelating agents, pH adjusting agents, buffering agents, additional solvents, nonionic surfactants, anionic surfactants, amphoteric surfactants, cationic surfactants, hydrotropes, skin conditioning agents, anti-foaming agents, builders, soil suspenders and anti-redeposition agents, brightening agents, radical scavengers, dyes, fragrances, rheology modifiers, corrosion inhibitors, softening agents, anti-static agents, anti-wrinkling agents, dye transfer inhibition/color protection agents, odor removal/odor capturing agents, preservatives, soil shielding/soil releasing agents, ultraviolet light protection agents, water repellency agents, insect repellency agents, anti-pilling agents, souring agents, mildew removing agents, film-forming agents, plasticizers, and allergicides.

Additional Antimicrobial Agents

In certain embodiments, the present compositions comprise an effective amount of at least one additional antimicrobial agent selected from the group consisting of inorganic or organic acids, anionic surfactants, amphoteric surfactants, quaternary ammonium compounds, aldehydes, biguanides, terpenes, essential oils, mineral acids, halogen compounds, and antimicrobial metals such as copper, and mixtures thereof. Organic acids include mono- or poly-carboxylic acids, including linear, branched, and cyclic carboxylic acids.

The additional antimicrobial agent can be present in an amount from about 0.005, 0.1, 0.5, 1, 1.5, 2, 2.5, 3, 3.5, 4, 4.5, 5, 6, 7, 8, 9, 10, 12, 15, 17, or 20 wt. %, and up to about 60, 50, 40, 30, 25, 15, 8, 3, or 0.5 wt. % in ready-to-use or concentrated solutions. The actual amount used will depend on the identity of the antimicrobial agent (different antimicrobial agents will have different strengths or activities and different solubilities) and whether the composition is a concentrate or a ready-to-use (RTU) composition.

Carboxylic Acids and Their Salts

At least one cyclic or linear, branched or unbranched, saturated or unsaturated, substituted or unsubstituted, mono-, di- or poly-carboxylic acids and salts thereof can be used in the present compositions. These can be chosen from C1 to C22 carboxylic acids and salts and isomers thereof. In some embodiments, the composition comprises at least one carboxylic acid and/or salt selected from the group consisting of C5 to C11 carboxylic acids and salts thereof. In other embodiments, the composition comprises at least one carboxylic acid and/or salt selected from the group consisting of C1 to C4 carboxylic acids and salts thereof. Examples of carboxylic acids and salts thereof that can be used in the present compositions include, but are not limited to, citric acid, formic acid, 2-furoic acid, salicylic acid, benzoic acid, mandelic acid, dimethylol propionic acid, sulfosalicylic acid, sulfosuccinic acid, glycolic acid, lactic acid, oxalic acid, malic acid, acetic acid, propionic acid, butanoic acid, pentanoic acid, hexanoic acid, heptanoic acid, octanoic acid, nonanoic acid, decanoic acid, undecanoic acid, dodecanoic acid, maleic acid, ascorbic acid, alpha-or-beta hydroxyacetic acid, neopentanoic acid, neoheptanoic acid, neononanoic acid, neodecanoic acid, malonic acid, succinic acid, glutaric acid, adipic acid, pimelic acid, suberic acid, and salts thereof. Most of these acids can be sourced from and found in nature. Examples include but are not limited to formic acid, benzoic acid, salicylic acid, 2-furoic acid, mandelic acid, acetic acid, gallic acid, malic acid, lactic acid, citric acid, glycolic acid, oxalic acid, propionic acid, maleic acid, ascorbic acid, malonic acid, succinic acid, and glutaric acid.

The at least one carboxylic acid and salts thereof can be selected from the group consisting of citric acid, formic acid, salicylic acid, 2-furoic acid, mandelic acid, acetic acid, dimethylol propionic acid, gallic acid, malic acid, lactic acid, benzoic acid, sulfosalicylic acid, sulfosuccinic acid, glycolic acid, oxalic acid, propionic acid, maleic acid, ascorbic acid, neopentanoic acid, malonic acid, succinic acid, glutaric acid, and salts thereof.

Example combinations of carboxylic acids and salts thereof include a selection of at least one compound from the group consisting of formic acid, salicylic acid, 2-furoic acid, mandelic acid, acetic acid, dimethylol propionic acid, gallic acid, malic acid, lactic acid, and salts thereof; combined with a selection of at least one compound from the group consisting of citric acid, benzoic acid, sulfosalicylic acid, sulfosuccinic acid, glycolic acid, oxalic acid, propionic acid, maleic acid, ascorbic acid, neopentanoic acid, malonic acid, succinic acid, glutaric acid, and salts thereof. Example combinations include a selection of at least one of salicylic acid, benzoic acid, mandelic acid, and 2-furoic acid; combined with at least one of citric acid and salts thereof. Example combinations include the following:

(i) 2-furoic acid and citric acid;
(ii) salicylic acid and citric acid; and
(iii) 2-furoic acid, salicylic acid, and citric acid.

The at least one acid and/or salt thereof can be present in a concentration of from about 0.02, 0.05, 0.1, 0.5, or 1 wt. % and up to about 60, 55, 50, 45, 40, 35, 30, 25, 20, 15, 13, 10, 8, 6, 4, or 3 wt. %. The actual amount of the acid and/or salt will depend on the identity of the compound and whether the composition is a concentrate or RTU solution. The amount of the compound in the RTU solution can be determined empirically for each antimicrobial agent through routine experimentation. Some of the factors affecting the effective concentration are specific activity of the antimicrobial agent against the specified pathogens, the molecular weight of thereof, and its solubility in the composition. The acid and/or salt will generally not be higher than 15 wt. % in ready-to-use solutions, or lower than 1 wt. % in concentrated solutions.

Nonionic Surfactants

Nonionic surfactants can be included to enhance the cleaning properties of the present compositions and/or to enhance solubility of other ingredients contained therein. Some have been found to synergistically enhance the antimicrobial activity of the compound of Formula 1.

Suitable nonionic surfactants include amine oxide surfactants (used at around neutral pH), alkoxylated surfactants such as alkoxylates made from ethylene oxide (EO), propylene oxide (PO), and butylene oxide (BO). Suitable alkoxylated surfactants include homo or copolymers or terpolymers, capped EO/PO/BO copolymers, alcohol alkoxylates, capped alcohol alkoxylates, mixtures thereof, or the like. Suitable alkoxylated surfactants that may be used as solvents include EO/PO block copolymers, such as the Pluronic™ and reverse Pluronic surfactants; alcohol alkoxylates such as Dehypon™ LS-54, and Dehypon™ LS-36 capped alcohol alkoxylates, such as Plurafac™ LF221 and Tegoten™ EC11. More specifically, the composition of the present specification can include an alkoxylated primary or secondary alcohol having from 8 to 18 carbon atoms reacted with from 2 to 12 moles of ethylene, and/or propylene, and/or butylene oxide. In an embodiment, the nonionic surfactant has from 3 to 18 moles of alkylene oxide, in another embodiment from 3 to about 10 moles of ethylene oxide (EO), and in yet another embodiment about 7 moles of EO. Examples include lauryl alcohol ethoxylated with 3 moles of ethylene oxide (EO), coco alcohol ethoxylated with 3 moles EO, stearyl alcohol ethoxylated with 5 moles EO, mixed $C_{12}$-$C_{15}$ alcohol ethoxylated with 7 moles EO, mixed secondary $C_{11}$-$C_{15}$ alcohol ethoxylated with 7 moles EO, mixed $C_9$-$C_{11}$ linear alcohol ethoxylated with 6 moles EO and the like. In some embodiments, the nonionic surfactant can have from 8 to 15 carbon atoms in the alkyl group. In an embodiment, the composition comprises the alcohol alkoxylates, particularly the alcohol ethoxylates and propoxylates, especially the mixed ethoxylates and propoxylates, particularly with 3-7 oxyethylene (EO) units and 3-7 oxypropylene (PO) units such as the alcohol Dehypon™ available from Cognis Corporation, having 5 EO units and 4 PO units.

The amine oxide surfactants can be selected from the group consisting of octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylamine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethy)amine oxide.

The concentration of the nonionic surfactant can be from about 0.02, 0.1, 0.2, 0.4, 0.6, 0.8, 1, 2.5, 5, 6.5, 10, or 20 wt. %, and up to about 60, 55, 50, 45, 40, 35, 30, 25, 20, 15, 8, 3, or 0.5 wt. %.

Anionic Surfactants

Anionic surfactants can enhance cleaning. Some also have antimicrobial properties such as alkyl aryl sulfonic acids (e.g. alkylbenzenesulfonic acids, alkyldiphenyloxide disulfonic acids), alkyl sulfuric acids, alkyl sulfonic acids, and alkyl phosphoric acid esters. Some have been found to synergistically enhance the antimicrobial activity of the compound of Formula 1.

Anionic surfactants that can be used in the present compositions include sulfuric acids such as alkyl ether sulfuric acids, the linear and branched primary and secondary alkyl sulfuric acids, alkyl ethoxysulfuric acids, fatty oleyl glycerol sulfuric acids, alkyl phenol ethylene oxide ether sulfuric acids, glucamine sulfuric acids, and alkylpolysaccharide sulfuric acids, such as the sulfuric acids of alkylpolyglucosides, alkyl poly(ethyleneoxy) ether sulfuric acids, sulfuric acid esters, and aromatic poly(ethyleneoxy) sulfuric acids such as the sulfuric acid or condensation products of ethylene oxide and nonyl phenol (usually having 1 to 6 oxyethylene groups per molecule). The salts of the above acids can also be used in the present compositions.

Anionic sulfonic acid surfactants that can be used include alkyl sulfonic acids, the linear and branched primary and secondary alkyl sulfonic acids, sulfonic acid esters, the aromatic sulfonic acids with or without substituents, including alkylbenzene sulfonic acids, and their salts.

Anionic carboxylic acids and salts thereof can also be used. These include alkyl carboxylic acids and their salts, alkanoic acids and their salts, ester carboxylic acids and their salts (e.g. alkyl succinates), alkyl ether carboxylic acids and their salts, and acylamino acids and their salts. Example anionic salts of carboxylic acids include alkyl ether carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable salts of acylamino acids include acylglutamates, acyl peptides, taurates (e.g. N-acyl taurates and fatty acid amides of methyl tauride), and the like.

Preferred anionic surfactants include $C_6$-$C_{24}$ alkylbenzene sulfonates; alkyl sarcosines and their salts, $C_6$-$C_{24}$ olefin sulfonates, $C_6$-$C_{24}$ paraffin sulfonates, cumene sulfonate, xylene sulfonate; $C_6$-$C_{24}$ alcohol sulfates (preferably $C_6$-$C_{12}$ alcohol sulfates), and $C_6$-$C_{24}$ alcohol ether sulfates having 1 to about 20 ethylene oxide groups, in either their acid or salt forms. Other suitable anionic surfactants include alkyl phosphonates, alkyl ether phosphonates, alkyl phosphates, alkyl ether phosphates, and phosphate esters, in either their acid or salt forms.

The concentration of the anionic surfactant can be from about 0.02, 0.1, 0.2, 0.4, 0.6, 0.8, 1, 2.5, 5, 6.5, 10, or 20 wt. %, and up to about 60, 55, 50, 45, 40, 35, 30, 25, 20, 15, 8, 3, or 0.5 wt. %.

Chelating Agents

Chelating agents can be included for the purpose of metal ion chelation, corrosion prevention, and in certain cases as antimicrobial agents or enhancers. These include, without limitation, 1-hydroxyethane-1,1-diphosphonic acid (HEDP, also referred to herein as etidronic acid), ethylenediaminetetraacetic acid (EDTA), glutamic acid diacetic acid (GLDA), methylglycine diacetic acid (MGDA), polymandelic acid, diethylenetriaminepentaacetic acid (DTPA), N-(hydroxyethyl)-ethylenediaminetriacetic acid (HEDTA), nitrilotriacetic acid (NTA), 2-hydroxyethyliminodiacetic acid (HEIDA), benzoic acid, aminobenzoic acid, citric acid, iminodisuccinic acid, polyaspartic acid, phosphoric acid, tripolyphosphate, amino tri(methylene phosphonic acid) (ATMP), diethylenetriaminepenta(methylene phosphonic acid), 2-hydroxy ethylimino bis(methylene phosphonic acid), ethylene diamine tetra(methylene phosphonic acid), hexamethylenediamine-tetra(methylene phosphonic) acid, and salts thereof.

When used, in certain embodiments, the chelating agents can be present in a concentration of from about 0.005, 0.1, 0.25, 0.5, 0.75, 1, 2, 3, 4, 5, 7, or 10 wt. % and up to about 20, 17.5, 15, 12.5, 8.5, or 2.5 wt. %.

pH Adjusting Agents and Buffering Agents

In aqueous antimicrobial compositions, at least one pH adjusting agent and/or buffering agent can be used in an amount effective to adjust and/or keep the pH of the solution to within the desired pH range. Examples include, without limitation, inorganic acids (e.g. phosphoric acid) and salts thereof, organic acids (e.g. citric acid, methane sulfonic acid, p-toluene sulfonic acid) and salts thereof, and alkaline agents (e.g. potassium hydroxide and sodium hydroxide).

The desired pH will depend on the specific application as will be apparent to the skilled person. For example, if an additional antimicrobial agent is used, the desired pH may be the value or range of values at which the additional antimicrobial agent is most effective, or to provide specific desired properties. The desired pH will vary from agent to agent and will be known to the skilled person having regard to information in the public domain. Therefore, aqueous compositions can have a pH ranging from 0 to 14. In some concentrated embodiments, the pH may also be below the value of zero (i.e. at a negative range).

In embodiments of ready-to-use compositions, the pH can range from about 0.1, 1, 1.5, 2, 2.5, 3, 3.5, 4, 4.5, 5, 5.5, 6, 6.5, 7, 7.5, or 8, and up to about 12, 11.5, 11, 10.5, 10, 9.5, 9, or 8.5. In embodiments of concentrated solutions, the pH can range from about 0 or 2.5 and up to about 11 or 14.

In embodiments wherein the composition contains no additional antimicrobial agents, the preferred pH of the composition would be from about 2.5 to 6.

The pH adjusting agent and/or buffering agent can be present in a total concentration of from about 0.01, 0.5, 1, 1.5, 2, 2.5, 3, 3.5, 5, or 7 wt. %, and up to about 50, 45, 40, 35, 30, 25, 20, 17, 15, 12, 10, 8, 6, 4, 2.2, 0.1, or 0.05 wt. %.

Hydrotropes

In certain embodiments, the solution or composition of the invention may include one or more hydrotropes for improving solubility and phase stability, such as salts of aryl and alkylaryl sulfonic acids such as xylene sulfonic acid, cumene sulfonic acid, and toluene sulfonic acid. Other hydrotropes include polyether phosphate esters, alkyl sulfates, alkyl and alkylaryl sultanates, diphenyloxide disulfonates, and benzoic acid salts.

When used, in certain embodiments, the hydrotrope can be present in a concentration of from about 0.1, 1, 3, 5, 10, or 20 wt. % and up to about 25, 15, 8, 4, or 1.5 wt. %.

It will be appreciated that certain hydrotropes can also be categorized as anionic or nonionic surfactants. The skilled person will appreciate the same compound may belong to more than one category and will understand the known categories to which the known compounds described herein belong.

Skin Conditioning Agents

In embodiments for use on skin, the solution may include an effective amount of at least one emollient, humectant or other skin conditioning agent, including but not limited to glycerin, polyglycerin, butylene glycol, glycerides, castor oil, allantoin, cationic polymers, lanolin and its derivatives, polyols and glycols such as glycerol, polyglycerol, sorbitol, mannitol, erythritol, xylitol, arabitol, ribitol, dulcitol, lactitol, maltitol, propylene glycol, hexylene glycol, ceramides, essential fatty acids such as linolenic acid, gamma-linolenic acid, linoleic acid, gamma-linoleic acid, tocopherols such as tocopheryl acetate, quaternised gums, quaternised polymers, glucose-ethers, vegetable oils, long chain fatty acids, long chain alcohols (e.g. cetyl alcohol), and phospholipids, and mineral oils.

When used, in certain embodiments, the skin conditioning agent can be present in a concentration of from about 0.01, 0.5, 2, 5, or 10 wt. %, and up to about 30, 25, 20, 15, 8, 4, or 1 wt %.

Other Ingredients

The present compositions can also include other ingredients such as anti-foaming agents, e.g. siloxanes, low-solubility oils, and low-HLB nonionic surfactants. In certain embodiments the other ingredients can be in a concentration of from about 0.001, 0.1, 0.5, 2, 4, 5, or 7 wt. %, and up to about 10, 8, 5, 4, or 3 wt. %.

In certain embodiments, builders can be present in a concentration of from about 0.01, 0.5, 2, 4, or 5 wt. %, and up to about 8, 3, 1, or 0.1 wt. %.

In certain embodiments, soil suspenders can be present in a concentration of from about 0.01, 0.5, 2, 5, or 10 wt. %, and up to about 15, 8, 4, 1, or 0.1 wt. %.

In certain embodiments, brighteners can be present in a concentration of from about 0.0005, 0.05, 0.1, 2, or 7 wt. %, and up to about 10, 5, 3, 1, or 0.01 wt. %.

In certain embodiments, radical scavengers and antioxidants can be present in a concentration of from about 0.005, 0.5, 1, or 5 wt. %, and up to about 15, 10, 3, 0.1, or 0.01 wt. %.

The invention is further described by the following non-limiting examples.

EXPERIMENTS AND TEST RESULTS

A number of solutions were prepared using the ingredients summarized in Table A and tested for their antimicrobial activity. The solutions and antimicrobial test results are summarized in Tables 1.0 to 4.0 (below). In these tables, the actual active concentration of each ingredient in terms of wt. % is shown.

TABLE A

| Molecule | Classification | Commercial Name (Manufacturer) | Active Content |
|---|---|---|---|
| Acetic acid | Antimicrobial agent; Carboxylic acid: Acidic pH adjusting agent | Glacial acetic acid (Sigma) | 100% |
| C8-C10 alkoxylated phosphate esters | Antimicrobial agent; Anionic surfactant | Multitrope ™ 1214 (Croda) | 100% |
| C9-C14 alkyl benzenesulfonic acids | Antimicrobial agent; Anionic surfactant | BioSoft ™ S-101 LS (Stepan) | >98% |
| Alkyl (C10-C16) benzenesulfonic acid | Antimicrobial agent; Anionic surfactant | BioSoft ™ S-101 (Stepan) | 95.50% |
| Alkyldimethylbenzyl ammonium chloride (ADBAC) | Antimicrobial agent; Quaternary ammonium compound; Cationic surfactant | BTC ™ 50 (Stepan) | 50% |
| Benzyl alcohol | Antimicrobial agent; Monohydroxy alcohol solvent | Benzyl alcohol (Univar) | 95-100% |

TABLE A-continued

| Molecule | Classification | Commercial Name (Manufacturer) | Active Content |
|---|---|---|---|
| Butyl-3-hydroxy butyrate | Solvent | Omnia™ solvent (Eastman) | >98% |
| C9-C11 ethoxylated alcohols | Nonionic surfactant | Tomadol™ 91-6 (Evonic) | 100% |
| Calcium hypochlorite | Antimicrobial agent; Chlorine compound | Calcium Hypochlorite (Sigma) | 100% |
| Capryleth-9 carboxylic acid | Antimicrobial agent; Anionic surfactant | Akypo™ LF 2 (Kao Chemicals) | >85% |
| Chlorhexidine gluconate | Antimicrobial agent | Chlorhexidine gluconate 20% (VWR) | 20% |
| Citric acid | Antimicrobial agent; Carboxylic acid; Acidic pH adjusting agent; Buffering agent | Anhydrous citric acid (Brenntag) | 95-100% |
| Cyanuric acid | Triazine; Chelating agent | Cyanuric acid (Sigma) | 100% |
| Didecyl dimethyl ammonium chloride (DDAC)/ADBAC | Antimicrobial agent; Quaternary ammonium compound mixture; compound; Cationic surfactant | BTC™ 1210 (Stepan) | 79-83% |
| Dimethyl succinate | Antimicrobial agent; Dibasic ester solvent | Dimethyl succinate (Sigma) | 100% |
| Dimethylol propionic acid | Antimicrobial agent; Carboxylic acid; Acidic pH adjusting agent | 2,2-Bis (hydroxymethyl) propionic acid (Sigma) | 100% |
| Ethanol | Antimicrobial agent; Monohydroxy alcohol solvent | Ethyl alcohol (VWR) | 100% |
| Ethylhexylglycerin | Antimicrobial agent; glycerol ether solvent | Sensiva™ SC 50 (Schulke) | >95% |
| Etidronic acid | Chelating agent; Acidic pH adjusting agent; buffering agent | Dequest™ 2010 (Italmach) | 60% |
| Formic acid | Antimicrobial agent; carboxylic acid | Reagent grade formic acid (Sigma) | >95% |
| 2-Furoic acid | Antimicrobial agent; Cyclic carboxylic acid | 2-furoic acid (Sigma) | 100% |
| Gallic acid | Antimicrobial agent; Cyclic carboxylic acid | Gallic acid (Derbiotech) | >98% |
| Glutaraldehyde | Antimicrobial agent; Aldehyde | Glutaraldehyde solution (Sigma) | 25% |
| Isopropyl alcohol | Antimicrobial agent: Monohydroxy alcohol solvent | Isopropyl alcohol (VWR) | 100% |
| Lactic acid | Antimicrobial agent; Carboxylic acid | Lactic acid (Sigma) | 80-90% |
| Lauramine oxide | Antimicrobial agent; Amphoteric surfactant | Ammonyx™ LO (Stepan) | 30% |
| Malic acid | Antimicrobial agent; Carboxylic acid | Malic acid (Tate & Lyle) | >95% |
| Mandelic acid | Antimicrobial agent; Cyclic carboxylic acid | Mandelic acid (Sigma) | 100% |
| Methyl methoxy benzoate | Antimicrobial agent; Ester; Fragrance | Methyl 2-methoxybenzoate (Sigma) | 100% |
| N,N-dimethyl 9-decenamide | Nonionic Surfactant and Solvent | Steposol™ Met-10U (Stepan) | 90-100% |
| N,N-dimethylalkylamide (C8-C10) | Nonionic Surfactant and Solvent | Steposol™ M-8-10 (Stepan) | 70-99% |
| N-butyl-gamma-butyrolactam | Antimicrobial agent; Solvent | Tamisolve™ NxG (Eastman) | >99.5% |
| N-octyl-gamma-butyrolactam | Nonionic Surfactant; Film forming agent | Surfadone™ LP-100 (Ashland) | >98% |
| Phosphoric acid | Antimicrobial agent; Mineral acid; Acidic pH adjusting agent; Buffering agent | Phosphoric acid FG (Brenntag) | 75% |
| Picolinic acid | Antimicrobial agent; Cyclic carboxylic acid; Chelating agent | pyridine-26-dicarboxylic (Alfa Aesar) | 95-100% |
| Potassium hydroxide (KOH) | Alkaline pH adjusting agent | Potassium hydroxide NF (Univar) | 45% |
| Salicylic acid | Antimicrobial agent; Cyclic carboxylic acid | Salicylic acid USP (Colombus) | >99% |

TABLE A-continued

| Molecule | Classification | Commercial Name (Manufacturer) | Active Content |
|---|---|---|---|
| Sodium capryloyl glutamate | Antimicrobial agent; Anionic surfactant | Plantapon ™ ACG HC (BASF) | 60% |
| Sodium cocoyl isethionate | Antimicrobial agent; Anionic surfactant | Hostapon ™ SCI 85 P (Clariant) | 85% |
| Sodium laureth sulfosuccinate | Antimicrobial agent; Anionic surfactant | Texapon ™ SB 3 KC (BASF) | 31-35% |
| Sodium lauroyl sarcosinate | Antimicrobial agent; Anionic surfactant | N-Lauroylsarcosine sodium salt (Sigma) | 100% |
| Sodium Salicylate | Antimicrobial agent; Salt of a cyclic carboxylic acid | Sodium Salicylate (Sigma) | >98% |

Example 1

TABLE 1.0

| | Solution | | |
|---|---|---|---|
| Ingredient | A | B | AA |
| N-butyl-gamma-butyrolactam | 4 | 7 | — |
| N-octyl-gamma-butyrolactam | — | — | 1 |
| C9-C11 ethoxylated alcohols | — | — | 2.2 |
| Deionized water | q.s. to 100 | q.s. to 100 | q.s. to 100 |
| $Log_{10}$ Reduction of *M. smegmatis*, 5 minutes contact time | 1.23 | 1.61 | 0 |
| $Log_{10}$ Reduction of *M. smegmatis*, 75 seconds contact time | Not tested | 0.11 | Not tested |

Solutions A, B and AA were prepared to test the antimicrobial activity of N-alkyl-gamma-butyrolactam, specifically N-butyl-gamma-butyrolactam and N-octyl-gamma-butyrolactam. These solutions were tested using the ASTM E2197-02 test method (5-minute contact time or 75 second contact time) without soil load, against hard-to-kill mycobacteria (*M. smegmatis*). The $log_{10}$ reductions in mycobacteria at a 5-minute contact time is shown in the second last row and demonstrate that N-butyl-gamma-butyrolactam surprisingly possesses antimicrobial activity, even against hard-to-kill mycobacteria. On the other hand, N-octyl-gamma-butyrolactam (Solution AA) possesses no antimicrobial activity under these test conditions. It is expected, based on these results, that N-alkyl-gamma-butyrolactams with an alkyl chain length greater than C6 will be ineffective in inactivating hard-to-kill microbes such as mycobacteria.

Solution B was also tested using ASTM E2197-02 test method (75 second contact time), without soil load, against mycobacteria (*M. smegmatis*) and achieved a $log_{10}$ reduction of 0.11 (shown in the last row of Table 1.0). This result can be compared with the results for the solutions in EXAMPLE 2 below to highlight the synergistic boost in antimicrobial efficacy of solution containing N-butyl-gamma-butyrolactam and an additional antimicrobial agent.

Example 2

Additional solutions were prepared to assess the antimicrobial activity of N-alkyl-gamma-butyrolactam, specifically N-butyl-gamma-butyrolactam, when combined with other antimicrobial agents in aqueous solution. These solutions are summarized in Tables 2.0, 2.1, and 22 below and tested using ASTM E2197-02 test method (75 second contact time), without soil load, against mycobacteria (*M. smegmatis*).

TABLE 2.0

| | Solution | | | | | | | |
|---|---|---|---|---|---|---|---|---|
| Ingredient | C | C1 | D | D1 | E | E1 | F | F1 |
| N-butyl-gamma-butyrolactam | — | 7 | — | 7 | — | 7 | — | 7 |
| Citric acid | 3 | 3 | — | — | — | — | — | — |
| Acetic acid | — | — | 5 | 5 | — | — | — | — |
| 2-Furoic acid | — | — | — | — | 0.5 | 0.5 | — | — |
| Alkyl (C10-C16) benzenesulfonic acid | — | — | — | — | — | — | 0.5 | 0.5 |
| Deionized water | q.s. to 100 | q.s. to 100 | q.s. to 100 | q.s. to 100 | q.s. to 100 | q.s. to 100 | q.s. to 100 | q.s. to 100 |
| $Log_{10}$ Reduction of *M. smegmatis*, 75 seconds contact time | 0.00 | 1.98 | 1.16 | 1.78 | 1.85 | 3.57 | 0.27 | 1.54 |

Solutions C, C1, D, D1, E, E1, F, and F1 contain different concentrations of antimicrobial carboxylic acids (citric acid, acetic acid, 2-furoic acid) or alkylbenzene sulfonic acid in aqueous solution. Solutions C1, D1, E1, and F1 also contain 7 wt. % N-butyl-gamma-butyrolactam. The results (when compared with the result for Solution B in Table 1.0), show a synergy between N-butyl-gamma-butyrolactam and the additives used in Table 2.0.

TABLE 2.1

| Ingredient | Solution | | | | | |
|---|---|---|---|---|---|---|
| | G | G1 | H | H1 | I | I1 |
| N-butyl-gamma-butyrolactam | — | 7 | — | 7 | — | 7 |
| Isopropyl alcohol | 25 | 25 | — | — | — | — |
| Ethanol | — | — | 25 | 25 | — | — |
| Dodecyldimethylammonium chloride (DDAC)/ADBAC | — | — | — | — | 0.3 | 0.3 |
| Potassium hydroxide (KOH) | — | — | — | — | pH to 11 | pH to 11 |
| Deionized water | q.s. to 100 | q.s. to 100 | q.s. to 100 | q.s. to 100 | q.s. to 100 | q.s. to 100 |
| $Log_{10}$ Reduction of *M. smegmatis*, 75 seconds contact time | 0.00 | 0.65 | 0.00 | 0.99 | 0.03 | 0.47 |

Solutions G to I1 contain different antimicrobial agents in aqueous solution. The desired pH of 11 for Solutions I and I1 was achieved using KOH. The pH of the other solutions was not measured. Solutions G1, H1, and I1 also contain 7 wt. % N-butyl-gamma-butyrolactam. The results (when compared with the result for Solution B in Table 1.0) show a synergy between N-butyl-gamma-butyrolactam and each additional antimicrobial agent used in Table 2.1.

TABLE 2.2

| Ingredient | Solution | | | |
|---|---|---|---|---|
| | J | J1 | K | K1 |
| N-butyl-gamma-butyrolactam | — | 7 | — | 7 |
| Calcium hypochlorite | 0.2 | 0.2 | — | — |
| DDAC and glutaraldehyde (1:1 ratio) | — | — | 0.4 | 0.4 |
| Potassium hydroxide (KOH) | pH to 11 | pH to 11 | Not measured | Not measured |
| Deionized water | q.s. to 100 | q.s. to 100 | q.s. to 100 | q.s. to 100 |
| $Log_{10}$ Reduction of *M. smegmatis*, 75 seconds contact time | 0.60 | 0.78 | 0.18 | 0.39 |

Solutions J, J1, K, and K1 contain an antimicrobial agent selected from calcium hypochlorite and DDAC/glutaraldehyde. Solutions J1 and K1 also contain 7 wt. % N-butyl-gamma-butyrolactam. The results (when compared with the result for Solution B in Table 1.0) show a synergy between N-butyl-gamma-butyrolactam and each of the antimicrobial agents used in Table 2.2.

Example 3

The 75 second contact time used in EXAMPLE 2 was selected to resemble conditions in which rapid evaporation of the solution may occur following application to a surface to be disinfected. The inventor has found that the synergy is still present, and an increase in microbial reduction is achieved, following an increase in contact time to 80 or 160 seconds, as shown in Tables 3.0-3.2, below, which list additional solutions containing N-butyl-gamma-butyrolactam and at least one additional antimicrobial agent.

TABLE 3.0

| Ingredient | Solutions | | | | | | | | | | | | | | | |
|---|---|---|---|---|---|---|---|---|---|---|---|---|---|---|---|---|
| | M | M1 | N | N1 | O | O1 | P | P1 | Q | Q1 | R | R1 | S | S1 | T | T1 |
| N-butyl-gamma-butyrolactam | 7.0 | — | 7.0 | — | 7.0 | — | 7.0 | — | 7.0 | — | 7.0 | — | 7.0 | — | 7.0 | — |
| C9-C11 ethoxylated alcohols | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Salicylic acid | 0.2 | 0.2 | — | — | — | — | — | — | — | — | — | — | — | — | — | — |
| Benzyl alcohol | — | — | 0.8 | 0.8 | — | — | — | — | — | — | — | — | — | — | — | — |
| Dimethyl succinate | — | — | — | — | 5.0 | 5.0 | — | — | — | — | — | — | — | — | — | — |
| Picolinic acid | — | — | — | — | — | — | 0.2 | 0.2 | — | — | — | — | — | — | — | — |
| Cyanuric acid | — | — | — | — | — | — | — | — | 0.2 | 0.2 | — | — | — | — | — | — |
| Mandelic acid | — | — | — | — | — | — | — | — | — | — | 0.4 | 0.4 | — | — | — | — |
| Dimethylol propionic acid | — | — | — | — | — | — | — | — | — | — | — | — | 0.4 | 0.4 | — | — |
| Gallic acid | — | — | — | — | — | — | — | — | — | — | — | — | — | — | 0.4 | 0.4 |
| Deionized water | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 |

TABLE 3.0-continued

| | Solutions | | | | | | | | | | | | | | | |
|---|---|---|---|---|---|---|---|---|---|---|---|---|---|---|---|---|
| | M | M1 | N | N1 | O | O1 | P | P1 | Q | Q1 | R | R1 | S | S1 | T | T1 |
| Potassium hydroxide or phosphoric acid | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 |
| $Log_{10}$ Reduction of *M. smegmatis*, 80 seconds contact time | 0.43 | — | 0.67 | — | 0.82 | — | 0.48 | — | 0.41 | — | 0.56 | — | 0.37 | — | 0.24 | — |
| $Log_{10}$ Reduction of *M. smegmatis*, 160 seconds contact time | 1.03 | 0.31 | 2.16 | 0.23 | 2.61 | 0.39 | 1.00 | 0.00 | 0.72 | 0.00 | 0.95 | 0.24 | 0.78 | 0.12 | 0.79 | 0.09 |

TABLE 3.1

| | Solutions | | | | | | | | | | | |
|---|---|---|---|---|---|---|---|---|---|---|---|---|
| | U | U1 | V | V1 | W | W1 | X | X1 | Y | Y1 | Z | Z1 |
| N-butyl-gamma-butyrolactam | 7 | — | 7 | — | 7 | — | 7 | — | 7 | — | 7 | — |
| C9-C11 ethoxylated alcohols | 0.1 | 0.1 | 0.1 | 0.1 | 0.1 | 0.1 | 0.1 | 0.1 | 0.1 | 0.1 | 0.1 | 0.1 |
| Malic acid | 0.40 | 0.40 | — | — | — | — | — | — | — | — | — | — |
| Lactic acid | — | — | 0.40 | 0.4 | — | — | — | — | — | — | — | — |
| Methyl methoxy benzoate | — | — | — | — | 0.40 | 0.40 | — | — | — | — | — | — |
| Capryleth-9 carboxylic acid | — | — | — | — | — | — | 0.23 | 0.23 | — | — | — | — |
| Sodium lauroyl sarcosinate | — | — | — | — | — | — | — | — | 0.15 | 0.15 | — | — |
| Butyl-3-hydroxy butyrate | — | — | — | — | — | — | — | — | — | — | 0.80 | 0.80 |
| Deionized water | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 |
| Potassium hydroxide or phosphoric acid | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 |
| $Log_{10}$ Reduction of *M. smegmatis*, 80 seconds contact time | 0.44 | — | 0.47 | — | 0.67 | — | 0.46 | — | 0.55 | — | 0.60 | — |
| $Log_{10}$ Reduction of *M. smegmatis*, 160 seconds contact time | 1.31 | 0.19 | 1.10 | 0.22 | 0.94 | 0.00 | 0.75 | 0.14 | 0.91 | 0.06 | 0.93 | 0.06 |

TABLE 3.2

| | Solutions | | | | | | | | | |
|---|---|---|---|---|---|---|---|---|---|---|
| | AA | AA1 | BB | BB1 | CC | CC1 | DD | DD1 | EE | EE1 |
| N-butyl-gamma-butyrolactam | 7 | — | 7 | — | 7 | — | 7 | — | 7 | — |
| C9-C11 ethoxylated alcohols | 0.1 | 0.1 | 0.1 | 0.1 | 0.1 | 0.1 | 0.1 | 0.1 | 0.1 | 0.1 |
| Ethylhexylglycerin | 0.30 | 0.30 | — | — | — | — | — | — | — | — |
| Acetic acid | — | — | 1.50 | 1.50 | — | — | — | — | — | — |
| N,N-dimethylalkylamide (C8-C10) | — | — | — | — | 0.30 | 0.30 | — | — | — | — |
| N,N-dimethyl 9-decenamide | — | — | — | — | — | — | 0.30 | 0.30 | — | — |
| Deionized water | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 |
| Potassium hydroxide or phosphoric acid | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 |
| $Log_{10}$ Reduction of *M. smegmatis*, 80 seconds contact time | — | — | — | — | — | — | — | — | 0.39 | — |

TABLE 3.2-continued

| | Solutions | | | | | | | | | |
|---|---|---|---|---|---|---|---|---|---|---|
| | AA | AA1 | BB | BB1 | CC | CC1 | DD | DD1 | EE | EE1 |
| $Log_{10}$ Reduction of M. smegmatis, 160 seconds contact time | 1.97 | 0.28 | 1.71 | 0.26 | 1.59 | 0.18 | 1.62 | 0.18 | 0.46 | 0.00 |

Solutions M through EE1 were prepared and tested using the ASTM E2197-02 test method, with soil load, against Mycobacterium M. smegmatis. Contact times of 80 or 160 seconds were employed as shown above. Solution EE contains C9-C11 ethoxylated alcohols (0.1 wt. %) and N-butyl-gamma-butyrolactam (7 wt. %). Phosphoric acid was added to achieve pH 2.5. Solution EE1 is the same as solution EE except that N-butyl-gamma-butyrolactam is absent. The results for Solution EE1 show that the C9-C11 ethoxylated alcohols (0.1 wt. %) do not contribute to antimicrobial efficacy. Comparing the results for Solution EE to the results for the other solutions M through to DD1 shows that the addition of N-butyl-gamma-butyrolactam leads to a synergistic boost in antimicrobial activity of all the solutions.

Example 4

Additional solutions were prepared similar to those shown in Tables 2.0 to 2.2, where each aqueous solution contained more than one known active ingredient, either with or without a N-alkyl-gamma-butyrolactam.

TABLE 4.0

| Solution: | Mixture of antimicrobial actives: | Antimicrobial synergy when combined with N-butyl-gamma-butyrolactam: |
|---|---|---|
| #1 | Citric acid (0.5 wt. %) + C9-C14 alkyl benzenesulfonic acids (0.25 wt. %) | Yes |
| #2 | DDAC (0.3 wt. %) + Isopropyl alcohol (32 wt. %) | Yes |
| #3 | Salicylic acid (0.3 wt. %) + Ethanol (35 wt. %) | Yes |
| #4 | Mandelic acid (0.6 wt. %) + 2-Furoic acid (0.6 wt. %) | Yes |
| #5 | DDAC (0.24 wt. %) 4-Glutaraldehyde (0.2 wt. %) + Chlorhexidine gluconate (0.2 wt. %) | Yes |

As shown in Table 4, similar observations were made where the addition of a N-alkyl-gamma-butyrolactam solvent, more specifically N-butyl-gamma-butyrolactam, led to a synergistic boost in the overall antimicrobial activity of each solution containing more than one known antimicrobial active ingredient. In the above solutions, the concentrations shown are actual active concentrations.

Example 5

Additional non-limiting exemplary solutions were prepared and are displayed below. In these solutions, the concentrations shown below are actual active concentrations.

Disinfectant Concentrate
  N-butyl-gamma-butyrolactam (45.0 wt. %)
  mixture of 09-C14 alkyl benzenesulfonic acids (8.0 wt. %)
  Salicylic acid (3.5 wt. %)
  deionized water (q.s. to 100)
  pH: 0.7
Ready-to-Use Topical Disinfectant Solution
  N-butyl-gamma-butyrolactam (6.0 wt. %)
  sodium capryloyl glutamate (2.0 wt. %)
  sodium cocoyl isethionate (1.8 wt. %)
  sodium lauroyl sarcosinate (0.2 wt. %)
  deionized water (q.s. to 100)
  pH: 3.6 (adjusted using citric acid)
Ready-to-Use Hard Surface Sanitizer
  N-butyl-gamma-butyrolactam (5.0 wt. %)
  lauramine oxide (1.0 wt. %)
  deionized water (q.s. to 100)
  pH: 2.6 (adjusted using phosphoric acid)
Ready-to-Use Hard Surface Disinfectant
  N-butyl-gamma-butyrolactam (7.0 wt. %)
  C8-C10 alkoxylated phosphate esters (0.4 wt. %)
  mixture of C9-C14 alkyl benzenesulfonic acids (0.2 wt. %)
  C9-C11 ethoxylated alcohols (0.15 wt. %)
  etidronic acid (0.2 wt. %)
  deionized water (q.s. to 100)
  pH: 2.3
Antimicrobial Hand Soap Solution
  N-butyl-gamma-butyrolactam (6.2 wt. %)
  capryleth-9 carboxylic acid (3.0 wt. %)
  disodium laureth sulfosuccinate (1.2 wt. %)
  ethanol (28.0 wt. %)
  salicylic acid (0.25 wt. %)
  deionized water (q.s. to 100)
  pH: 2.8

Example 6

Solutions X1 to X27 were prepared using certain compounds of Table A (above). All solutions contained deionized water, q.s. to 100, and a pH adjuster (KOH or $H_3PO_4$) to achieve a pH of 2.5. The solutions were tested for their antimicrobial activity using the ASTM E2197-02 test method against wet Staphylococcus Aureus bacterial inoculums. Further details of the solutions and results of the experiments are summarized in Tables 5-9 (below), wherein the amount of each compound is expressed in terms of wt. % of the raw material used. Actual amounts of the compounds in the solutions can be determined with reference to Table A. Note that "TNTC" means too numerous to count (log reduction<0.19) and that "NT" means not tested.

TABLE 5

| Compound | X1 | X2 | X3 |
|---|---|---|---|
| N-butyl-gamma-butyrolactam | 0.1 | 0.25 | 0.5 |
| KOH or $H_3PO_4$ | | pH to 2.5 | |
| Log Base Ten Reduction of *Staph. aureus*, 10 minutes contact time | 0.22 | 0.48 | 0.63 |
| Log Base Ten Reduction of *Staph. aureus*, 5 minutes contact time | TNTC (<0.19) | TNTC (<0.19) | 0.19 |

TABLE 6

| Compound | X4 | X5 | X6 | X7 | X8 | X9 | X10 | X11 |
|---|---|---|---|---|---|---|---|---|
| N-butyl-gamma-butyrolactam | 0.5 | — | 0.5 | — | 0.5 | — | 0.5 | — |
| Sodium Salicylate | 0.05 | 0.05 | — | — | — | — | — | — |
| Furoic acid | — | — | 0.4 | 0.4 | — | — | — | — |
| Mandelic acid | — | — | — | — | 0.4 | 0.4 | — | — |
| Malic acid | — | — | — | — | — | — | 0.4 | 0.4 |
| KOH or $H_3PO_4$ | | | | pH to 2.5 | | | | |
| Log Base Ten Reduction of *Staph. aureus*, 10 minutes contact time | ≥5.91 | NT | ≥5.91 | NT | ≥5.91 | NT | 1.81 | 0.5 |
| Log Base Ten Reduction of *Staph. aureus*, 5 minutes contact time | 4.83 | 2.83 | 2.70 | 0.61 | 1.59 | 0.50 | NT | NT |

TABLE 7

| Compound | X12 | X13 | X14 | X15 | X16 | X17 | X18 | X19 |
|---|---|---|---|---|---|---|---|---|
| N-butyl-gamma-butyrolactam | 0.5 | — | 0.5 | — | 0.5 | — | 0.5 | — |
| Glacial Acetic acid | 1 | 1 | — | — | — | — | — | — |
| Dimethylol propionic acid | — | — | 0.5 | 0.5 | — | — | — | — |
| Gallic acid | — | — | — | — | 0.5 | 0.5 | — | — |
| Lactic acid | — | — | — | — | — | — | 0.5 | 0.5 |
| KOH or $H_3PO_4$ | | | | pH to 2.5 | | | | |
| Log Base Ten Reduction of *Staph. aureus*, 10 minutes contact time | 3.11 | 1.51 | 3.27 | 0.99 | ≥5.38 | 1.54 | ≥5.38 | 2.94 |

TABLE 8

| Compound | X20 | X21 | X22 | X23 | X24 | X25 | X26 | X27 |
|---|---|---|---|---|---|---|---|---|
| N-butyl-gamma-butyrolactam | 0.1 | 0.1 | 0.1 | 0.1 | 0.1 | 0.1 | 0.1 | 0.1 |
| Sodium Salicylate | 0.05 | — | — | — | — | — | — | — |
| Furoic acid | — | 0.4 | — | — | — | — | — | — |
| Mandelic acid | — | — | 0.4 | — | — | — | — | — |
| Malic acid | — | — | — | 0.4 | — | — | — | — |
| Dimethylol propionic acid | — | — | — | — | 0.5 | — | — | — |
| Gallic acid | — | — | — | — | — | 0.5 | — | — |
| Lactic acid | — | — | — | — | — | — | 0.5 | — |
| Glacial Acetic acid | — | — | — | — | — | — | — | 1 |
| KOH or $H_3PO_4$ | | | | pH to 2.5 | | | | |
| Log Base Ten Reduction of *Staph. aureus*, 10 minutes contact time | NT | NT | NT | 0.70 | 0.64 | 1.65 | 3.12 | 1.82 |
| Log Base Ten Reduction of *Staph. aureus*, 5 minutes contact time | 2.69 | 0.68 | 0.52 | NT | NT | NT | NT | NT |

In the above tables, the contact time for each test was selected to allow for a determination of the presence or absence of a synergy. For example, when a contact time of 10 minutes led to complete inactivation of microbes, a 5 minute contact time was used to achieve a precise or quantifiable result (see Table 6). In Table 8, the contact time was selected to allow for a meaningful comparison to be made with the results of Tables 5, 6 and 7.

The results in Tables 5, 6 and 7 show that N-butyl-gamma-butyrolactam at 0.5 wt. % (solution X3) acts synergistically with the compounds tested, namely, a. sodium salicylate at 0.05 wt. % (the result for solution X3 plus the result for solution X5 is less than the result for solution X4 at 5 minutes contact time),
b. furoic acid at 0.4 wt. % (the result for solution X3 plus the result for solution X7 is less than the result for solution X6 at 5 minutes contact time),
c. mandelic acid at 0.4 wt. % (the result for solution X3 plus the result for solution X9 is less than the result for solution X8 at 5 minutes contact time),
d. malic acid at about 0.4 wt. % (the result for solution X3 plus the result for solution X11 is less than the result for solution X10 at 10 minutes contact time),
e. glacial acetic acid at 1 wt. % (the result for solution X3 plus the result for solution X13 is less than the result for solution X12 at 10 minutes contact time),
f. dimethylol propionic acid at 0.5 wt. % (the result for solution X3 plus the result for solution X15 is less than the result for solution X14 at 10 minutes contact time),
g. gallic acid at about 0.5 wt. % (the result for solution X3 plus the result for solution X17 is less than the result for solution X16 at 10 minutes contact time), and
h. lactic acid at about 0.5 wt. % (the result for solution X3 plus the result for solution X19 is less than the result for solution X18 at 10 minutes contact time).

The results in Tables 5, 6, 7, and 8 show that there is no synergy between 0.1 wt. % N-butyl-gamma-butyrolactam (solution X1) in combination with—
i. sodium salicylate at 0.05 wt. % (the result for X1 plus the result for X5 is not less than the result for X20 at 5 minutes contact time),
j. furoic acid at 0.4 wt. % (the result for X1 plus the result for X7 is not clearly less than the result for X21 at 5 minutes contact time),
k. mandelic acid at 0.4 wt. % (the result for X1 plus the result for X9 is not clearly less than the result for X22 at 5 minutes contact time),
l. malic acid at about 0.4 wt. % (the result for X1 plus the result for X11 is not less than the result for X23 at 10 minutes contact time),
m. dimethylol propionic acid at 0.5 wt. % (the result for X1 plus the result for X15 is not clearly less than the result for X24 at 10 minutes contact time),
n. gallic acid at about 0.5 wt. % (the result for X1 plus the result for X17 is not less than the result for X25 at 10 minutes contact time),
o. lactic acid at about 0.5 wt. % (the result for X1 plus the result for X19 is not less than the result for X26 at 10 minutes contact time), and
p. glacial acetic acid at 1 wt. % (the result for X1 plus the result for X13 is not less than the result for X27 at 10 minutes contact time).

Table 5 also shows that N-butyl-gamma-butyrolactam on its own at a concentration of 0.25 wt. % or higher (solutions X2 and X3) is effective to reduce the microbial load by at least 50% at 10 minutes contact time. On the other hand, solution X1 did not reduce the microbial load by at least 50% at 10 minutes contact time. A 50% reduction of microbial load on a surface is equivalent to approximately 0.301 log base ten reduction. A reference chart is included below which (among other things) correlates log reduction values with percent reduction values:

| Log Reduction | Number of CFUs Remaining | Percentage Reduction |
|---|---|---|
| 0 log | 1,000,000 | 0% |
| 1 log | 100,000 | 90% |
| 2 log | 10,000 | 99% |
| 3 log | 1,000 | 99.9% |
| 4 log | 100 | 99.99% |
| 5 log | 10 | 99.999% |
| 6 log | 1 | 99.9999% |

TABLE 9

| Compound | X1 | X3 | X28 | X29 | X30 | X31 | X32 | X33 |
|---|---|---|---|---|---|---|---|---|
| N-butyl-gamma-butyrolactam | 0.5 | 0.1 | 0.5 | — | 0.5 | — | 0.1 | 0.1 |
| Formic acid | — | — | 0.3 | 0.3 | 0.1 | 0.1 | 0.3 | 0.1 |
| KOH or $H_3PO_4$ | | | | pH to 2.5 | | | | |
| Log Base Ten Reduction of *Staph. aureus*, 10 minutes contact time | 0.63 | 0.22 | ≥5.77 | 2.94 | 2.39 | 1.61 | 3.34 | 1.66 |

The above tests explore the lower concentration ranges at which formic acid and its salts+C3-C5 N-alkyl-gamma-butyrolactam may be synergistic. The results in Table 9 show (at least) that 0.5 wt. % N-butyl-gamma-butyrolactam is synergistic with formic acid at 0.3 wt. %.

Example 7

Table 10 summarizes solutions X34-X41, which were prepared using certain compounds of Table A (above). All solutions contained deionized water, q.s. to 100. The pH of solutions X37 and X39-X41 was adjusted using KOH to the values indicated in Table 10. The solutions were tested for their antimicrobial activity using the ASTM E2197-02 test method against wet *M. Smegmatis* mycobacterial inoculums. Further details of the solutions and results of the experiments are summarized also in Table 10 (below), wherein the amount of each compound is expressed in terms of wt. % of the raw material used. Actual amounts of the compounds in the solutions can be determined with reference to Table A.

TABLE 10

| | X34 | X35 | X36 | X37 | X38 | X39 | X40 | X41 |
|---|---|---|---|---|---|---|---|---|
| N-butyl-gamma-butyrolactam | | | | 6.8 | | | | |
| C9-C11 ethoxylated alcohols | | | | 0.1 | | | | |
| Citric acid | — | 1 | 2 | 2 | 3 | 3 | 2 | — |
| Furoic acid | — | — | — | — | — | — | 0.35 | 0.35 |
| pH value | 4.99 | 2.29 | 2.13 | 3.0 | 2.1 | 3.0 | 2.5 | 2.5 |
| Log Base Ten Reduction of M. Smegmatis, 40 seconds contact time | 0.77 | 2.71 | 3.27 | 2.19 | 3.8 | 3.71 | 4.8 | 0.98 |

The above results, when compared to the result for Solution C (Table 2.0 above), demonstrate that:
1. an increase in concentration of citric acid leads to an increase in the synergistic efficacy in the presence of the N-butyl-gamma-butyrolactam at 6.8 wt. % (see solutions X35, X36, and X38);
2. the increase in the synergistic efficacy is not due to acidification (compare solution X37 and X39 which both have a pH of 3.0); and
3. the increase in the synergistic efficacy is further increased synergistically by the addition of a cyclic carboxylic acid, in this case, furoic acid, at 0.35 wt. % (compare the result for solution X40 with the result for each of X36 and X41).

The skilled person will appreciate that variations to the embodiments described above can be made without departing from the scope of the invention described and claimed herein. For example, concentrations of synergistic antimicrobial agents can be increased without eliminating the synergies herein demonstrated. It is expected that, at higher concentrations, the effectiveness of antimicrobial agents will increase. It is also expected that any synergy demonstrated at lower concentrations will not disappear when the concentration of synergistic compounds are increased, or if the ratio of synergistic compounds are changed at any higher concentrations.

The foregoing description of embodiments is by way of example only and is not intended to limit the scope of the invention as herein described and claimed.

The invention claimed is:
1. An antimicrobial composition comprising:
  (a) an antimicrobially synergistic combination of compounds consisting of:
    (i) from about 0.25% wt. of a first an antimicrobial agent consisting of at least one compound according to Formula 1:

[Formula 1]
    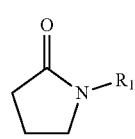

wherein R1 is a branched or unbranched, saturated or unsaturated, unsubstituted C3 to C5 alkyl chain or a C3 alkyl chain substituted with a methoxy group;
    (ii) an effective amount of at least one solvent selected from the group consisting of alcohols, dibasic esters, glyceryl ethers, and butyl 3-hydroxybutyrate; and
    (iii) optionally, at least one additional antimicrobial agent selected from the group consisting of carboxylic acids and salts thereof, anionic surfactants, amphoteric surfactants, nonionic surfactants, cationic surfactants, quaternary ammonium compounds, aldehydes, biquanides, mineral acids, antimicrobial metals, and mildew removing agents;
  (b) a diluent, q.s. to 100;
  wherein the at least one compound according to Formula 1 is effective to reduce the number of microbes on a surface by at least 50% when an effective amount of the antimicrobial composition is applied to the surface for a contact time of 10 minutes, and wherein the antimicrobial composition is substantially free of peroxygen compounds, antibiotics, N-methyl pyrrolidone (NMP), N-ethyl pyrrolidone (NEP), and chloroacetamide.

2. The antimicrobial composition of claim 1, wherein said at least one compound according to Formula 1 is selected from the group consisting of N-butyl-gamma-butyrolactam, N-isobutyl-gamma-butyrolactam, and N-methoxypropyl-gamma-butyrolactam.

3. The antimicrobial composition of claim 1, wherein said diluent is water.

4. The antimicrobial composition of claim 3, further comprising an effective amount of a pH adjusting agent.

5. The antimicrobial composition of claim 1, wherein the at least one solvent is selected from the group consisting of C1-C8 alcohols, cyclic alcohols, dialkyl succinates, glyceryl ethers, and butyl 3-hydroxybutyrate.

6. The antimicrobial composition of claim 1, wherein the at least one solvent is selected from the group consisting of ethanol, propanol, butanol, isopropyl alcohol, benzyl alcohol, dimethyl succinate, ethylhexylglycerin, and butyl 3-hydroxybutyrate.

7. The antimicrobial composition of claim 1, wherein the carboxylic acids and salts thereof are selected from the group consisting of formic acid, benzoic acid, salicylic acid, 2-furoic acid, mandelic acid, acetic acid, dimethylol propionic acid, gallic acid, malic acid, lactic acid, citric acid, sulfosalicylic acid, sulfosuccinic acid, glycolic acid, oxalic acid, propionic acid, maleic acid, ascorbic acid, neopentanoic acid, malonic acid, succinic acid, glutaric acid, and salts thereof.

8. The antimicrobial agent of claim 7, wherein at least one of citric acid and salts thereof is present.

9. The antimicrobial composition of claim 7, wherein at least one of formic acid, benzoic acid, salicylic acid, 2-furoic acid, mandelic acid, lactic acid, glycolic acid, and salts thereof, is present.

10. The antimicrobial composition of claim 1, wherein the anionic surfactants are selected from the group consisting of alkyl sulfuric acids, alkyl ether sulfuric acids, alkyl sulfonic acids, alkyl aryl sulfonic acids, alkyl phosphoric acid esters, alkyl carboxylic acids, alkyl ether carboxylic acids, acylamino acids, and salts thereof.

11. The antimicrobial composition of claim 1, further comprising an effective amount of at least one ingredient selected from the group consisting of carbonate solvents, chelating agents, stabilizing agents, buffering agents, hydrotropes, skin conditioning agents, anti-foaming agents, builders, soil suspenders, anti-redeposition agents, brightening agents, radical scavengers, dyes, fragrances, rheology modifiers, emulsifiers, corrosion inhibitors, softening agents, anti-static agents, anti-wrinkling agents, dye transfer inhibition agents, color protection agents, odor removal agents, odor capturing agents, soil shielding agents, soil releasing agents, ultraviolet light protection agents, water repellency agents, insect repellency agents, anti-pilling agents, souring agents, film-forming agents, plasticizers, and allergicides.

12. The antimicrobial composition of claim 11, wherein said at least one ingredient is selected from the group consisting of chelating agents, buffering agents, skin conditioning agents, hydrotropes, corrosion inhibitors, and fragrances.

13. An antimicrobial composition comprising:
(a) an antimicrobially synergistic combination of compounds consisting of:
(i) from about 0.25% wt. of an antimicrobial agent consisting of at least one compound according to Formula 1:

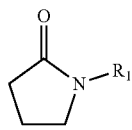

[Formula 1]

wherein R1 is a branched or unbranched, saturated or unsaturated, unsubstituted C3 to C5 alkyl chain or a C3 alkyl chain substituted with a methoxy group;
(ii) an effective amount of at least one solvent selected from the group consisting of ethanol, propanol, butanol, isopropyl alcohol, benzyl alcohol, dimethyl succinate, ethylhexylglycerin, and butyl 3-hydroxybutyrate;
(iii) an effective amount of at least one of citric acid and salts thereof; and
(iv) optionally, at least one additional antimicrobial agent selected from the group consisting of carboxylic acids and salts thereof other than those recited in (iii), anionic surfactants, amphoteric surfactants, nonionic surfactants, cationic surfactants, quaternary ammonium compounds, phenols, aldehydes, biguanides, mineral acids, glyceryl ethers other than those recited in (ii), phenethyl alcohol, phenoxyethanol, cyclopentylmethanol, dimethyl adipate, 2-butoxyethanol, diethylene glycol monobutyl ether, ethylene carbonate, propylene carbonate, butylene carbonate, glycerin carbonate, antimicrobial metals, and mildew removing agents;
(b) a diluent, q.s. to 100;
wherein at least one compound according to Formula 1 is effective to reduce the number of microbes on a surface by at least 50% when aneffective amount of the antimicrobial composition is applied to the surface for a contact time of 10 minutes, and wherein the antimicrobial composition is substantially free of peroxygen compounds, antibiotics, N-methyl pyrrolidone (NMP), N-ethyl pyrrolidone (NEP), and chloroacetamide.

14. The antimicrobial composition of claim 13, wherein said at least one compound according to Formula 1 is selected from the group consisting of N-butyl-gamma-butyrolactam, N-isobutyl-gamma-butyrolactam, and N-methoxypropyl-gamma-butyrolactam.

15. The antimicrobial composition of claim 13, wherein said diluent is water.

16. The antimicrobial composition of claim 15, further comprising an effective amount of a pH adjusting agent.

17. The antimicrobial composition of claim 13, wherein the carboxylic acids and salts thereof are selected from the group consisting of salicylic acid, 2-furoic acid, mandelic acid, benzoic acid, formic acid, glycolic acid, lactic acid and salts thereof.

18. The antimicrobial composition of claim 13, wherein the anionic surfactants are selected from the group consisting of alkyl sulfuric acids, alkyl ether sulfuric acids, alkyl sulfonic acids, alkyl aryl sulfonic acids, alkyl phosphoric acid esters, alkyl carboxylic acids, alkyl ether carboxylic acids, acylamino acids, and salts thereof.

19. The antimicrobial composition of claim 13, further comprising at least one ingredient selected from the group consisting of carbonate solvents, chelating agents, stabilizing agents, buffering agents, hydrotropes, skin conditioning agents, anti-foaming agents, builders, soil suspenders, anti-redeposition agents, brightening agents, radical scavengers, dyes, fragrances, rheology modifiers, emulsifiers, corrosion inhibitors, softening agents, anti-static agents, anti-wrinkling agents, dye transfer inhibition agents, color protection agents, odor removal agents, odor capturing agents, soil shielding agents, soil releasing agents, ultraviolet light protection agents, water repellency agents, insect repellency agents, anti-pilling agents, souring agents, film-forming agents, plasticizers, and allergicides.

* * * * *